(12) United States Patent
Bercovich et al.

(10) Patent No.: US 9,820,836 B2
(45) Date of Patent: Nov. 21, 2017

(54) MEDICAL DEVICE FOR TREATMENT OF URINARY INCONTINENCE IN FEMALES

(75) Inventors: Eyal Bercovich, Haifa (IL); Ronen Raveh, Ramat Yishay (IL)

(73) Assignee: GYNAMICS WOMEN'S HEALTH LTD., Ramat Yishay (IL)

( * ) Notice: Subject to any disclaimer, the term of this patent is extended or adjusted under 35 U.S.C. 154(b) by 182 days.

(21) Appl. No.: 13/637,284

(22) PCT Filed: Mar. 31, 2011

(86) PCT No.: PCT/IL2011/000288
§ 371 (c)(1),
(2), (4) Date: Nov. 8, 2012

(87) PCT Pub. No.: WO2011/121591
PCT Pub. Date: Oct. 6, 2011

(65) Prior Publication Data
US 2013/0053627 A1  Feb. 28, 2013

Related U.S. Application Data

(60) Provisional application No. 61/428,231, filed on Dec. 30, 2010, provisional application No. 61/320,328, filed on Apr. 2, 2010.

(51) Int. Cl.
*A61F 2/04* (2013.01)
*A61F 2/00* (2006.01)

(52) U.S. Cl.
CPC .................... *A61F 2/005* (2013.01)

(58) Field of Classification Search
CPC ....................................................... A61F 2/005
(Continued)

(56) References Cited

U.S. PATENT DOCUMENTS

| 4,920,986 A | 5/1990 | Biswas |
| 5,007,894 A | 4/1991 | Enhorning |

(Continued)

FOREIGN PATENT DOCUMENTS

| WO | 1996001084 | 1/1996 |
| WO | 2000067662 | 11/2000 |

(Continued)

*Primary Examiner* — Navin Natnithithadha
*Assistant Examiner* — Sunita Reddy
(74) *Attorney, Agent, or Firm* — Roach Brown McCarthy & Gruber, P.C.; Kevin D. McCarthy

(57) ABSTRACT

An intra-vaginal device for controlling urinary incontinence, designed to be placed longitudinally in the vagina, includes: a. a deformable distal portion, placed in the subvesical region of the vagina, characterized by a deformable state and an un-deformable state; b. a deformable proximal portion placed in the sub-urethral portion of the vagina, characterized by a deformable state and an un-deformable state; c. a deformation controlling mechanism interconnecting said distal portion and said proximal portion, adapted to reversibly transform said distal portion and said proximal portion form said deformable state to said un-deformable state; and from said un-deformable state to said deformable state; wherein upon predetermined amount of intra-vaginal pressure applied on said proximal pressure, said deformation controlling mechanism is adapted to transform proximal portion from said un-deformable state to said deformable state such that pressure is applied on said urethra.

11 Claims, 12 Drawing Sheets

(58) Field of Classification Search
USPC .................. 600/29–31, 37; 128/897–899
See application file for complete search history.

(56) References Cited

U.S. PATENT DOCUMENTS

| | | | |
|---|---|---|---|
| 5,609,559 | A | 3/1997 | Weitzner |
| 5,611,768 | A * | 3/1997 | Tutrone, Jr. ............... 600/29 |
| 5,795,288 | A | 8/1998 | Cohen et al. |
| 6,110,099 | A * | 8/2000 | Benderev .................. 600/30 |
| 6,135,945 | A * | 10/2000 | Sultan ..................... 600/30 |
| 6,189,535 | B1 | 2/2001 | Enhorning |
| 7,736,298 | B2 | 6/2010 | Guerquin et al. |
| 7,771,344 | B2 | 8/2010 | Ziv |
| 8,652,026 | B2 * | 2/2014 | Zunker et al. ............. 600/29 |
| 2004/0158122 | A1 * | 8/2004 | Guerquin .................. 600/29 |
| 2007/0244352 | A1 | 10/2007 | Ziv |
| 2007/0250132 | A1 * | 10/2007 | Burnett ............... A61F 5/003 607/40 |
| 2008/0033231 | A1 * | 2/2008 | Bartning et al. .......... 600/29 |
| 2008/0281149 | A1 | 11/2008 | Sinai et al. |
| 2009/0105527 | A1 | 4/2009 | Connors et al. |
| 2009/0247817 | A1 | 10/2009 | Forsell |

FOREIGN PATENT DOCUMENTS

| | | |
|---|---|---|
| WO | WO 2004/103213 A1 | 12/2004 |
| WO | WO 2011/121591 A2 | 10/2011 |

\* cited by examiner

MEDICAL DEVICE FOR TREATMENT OF URINARY INCONTINENCE IN FEMALES

FIELD OF THE INVENTION

This invention relates in general to means for treating urinary incontinence in females. In particular, it relates to devices that are inserted into the vagina and are activated by intra vaginal, intra-abdominal or contraction of the pelvic floor muscles to create a transient pressure on the urethra.

BACKGROUND

Urinary incontinence (UI), the involuntary loss of urine, is estimated to affect approximately one in three adult women. Due to such factors as pregnancy and childbirth, menopause, and the structure of the female urinary tract, UI is twice as prevalent in women as in men. UI can also arise from such causes as neurologic injury, birth defects, stroke, multiple sclerosis, and the physical problems associated with aging. UI can run the gamut from slightly bothersome to completely debilitating: some women suffering from UI lose a few drops of urine during activities such as running or coughing, while others may feel a strong, sudden urge to urinate just before losing a large amount of urine. For some women suffering from UI, the risk of public embarrassment can keep them from enjoying activities with family and friends.

Stress urinary incontinence (SUI), also known as effort incontinence, is typified by loss of small amounts of urine associated with movements that increase the intra-abdominal pressure, thereby increasing the pressure on the bladder. If the support provided to the urethra by the fascia of the pelvic is insufficient, then at times of increased intra-abdominal pressure, for example, during movements that increase the intra-abdominal pressure and hence the pressure on the urinary bladder such as coughing, laughing, sneezing, and exercise, the urethra can move downward, allowing urine to pass.

The anatomic structures that prevent SUI in healthy women can be divided into two systems, a sphincteric system and a support system. The action of the vesical neck and urethral sphincteric systems at rest constrict the urethral lumen and keep urethral pressure higher than the pressure in the urinary bladder. The striated urogenital sphincter, the smooth muscle sphincter in the vesical neck, and the circular and longitudinal smooth muscle of the urethra all contribute to the pressure that at least partially closes the urethra. The mucosal and vascular tissues that surround the lumen provide a hermetic seal, and the connective tissues in the urethral wall also aid coaptation. Decreases in striated muscle fibers occur with age. The supportive hammock under the urethra and vesical neck provides a firm backstop against which the urethra is compressed during increases in abdominal pressure to maintain a sufficient urethral pressure to keep it closed as the pressure in the urinary bladder increases. The stiffness of this supportive layer is presumed to be important to the degree to which compression of the urethra can occur.

While SUI is more common in older women than in younger women, it is not an inevitable consequence of aging. As the population ages, there is an increasing need for nonsurgical methods for treating SUI. One such method is to place an insert in the vagina which presses against the urethra, providing support for the urethro-vaginal myofascial area and thereby preventing involuntary loss of urine. One approach to the construction of such an insert is exemplified by the devices disclosed in U.S. Pat. No. 7,771,344 and in U.S. patent application Ser. No. 10/598,872, now U.S. Pat. No. 8,727,961. These devices comprise an insert that provides a constant pressure to the urethra, preventing SUI. The constant pressure provided by such devices is their primary disadvantage. Increased pressure on the urethra to prevent incontinence is only necessary during the brief intervals of increased intra-abdominal pressure described above.

A second approach is taken in the design of the device disclosed in U.S. Pat. No. 7,736,298. This device comprises two ends, a distal deformable end and a proximal end that cannot be deformed. The device is inserted such that the distal end is adjacent to the urinary bladder. When the bladder is full, distal end is deflected, and the leverage provided by the increased pressure from the bladder deflects proximal end in the opposite direction, closing the urethra. While this device has the advantage that it is activated only when the bladder pressure is high, it also has the disadvantage that it is essentially rigid and provides a constant pressure to the urethra as long as bladder is full and provides a constant pressure to the urethra as long as bladder is full. This rigidity means that the device must be provided in a variety of sizes, because one standard size is unlikely to fit all women.

A third approach is to design devices that are partially or wholly inflatable such that pressure is applied to the urethra only when the device is in its inflated state. Examples of such devices are the commercially available "Inflatoball" sold by Cooper Surgical and devices such as those disclosed in U.S. Pat. No. 4,920,986 and U.S. Pat. No. 6,189,535. In these devices, however, a source of air external to the body is necessary, or means external to the body (e.g. a syringe) are necessary to deflate the device. Furthermore, these devices must also be provided in a variety of sizes so that any individual woman can be guaranteed one that has the proper fit.

Thus, a device for treating urinary incontinence in females that uses hydraulic means (e.g. inflation or deflation of a portion of the device) to provide the necessary pressure, that is truly self-contained once it is inserted, and that can be adjusted to fit the body of a specific user, remains a long-felt and unmet need. In addition, there remains a long-felt and unmet need for a device that can act both as a means for preventing urinary incontinence and as a means for rehabilitating a female suffering from SUI by increasing the strength of the pelvic floor muscles.

SUMMARY OF THE INVENTION

The invention herein disclosed is designed to meet these needs. The device comprises a dynamic mechanism that keeps a baseline pressure that is increased upon triggering by a rise in the intra-vaginal pressure (which in term is correlated to both intra-abdominal pressure and to contraction of the pelvic floor muscles). The dynamic response not only creates a barrier to flow of urine through the urethra but also assists in returning to the bladder any small volume of urine that may have escaped therefrom. The device of the present invention thus mimics the natural mechanism of the body described above. Furthermore, since there is no need in a dynamic system for constant high pressure on the vaginal wall, the risk of tissue injury is significantly reduced.

In addition to automatic activation of the device upon a transient rise in intra-vaginal pressure caused by a transient rise in intra-abdominal pressure (e.g. due coughing or sneezing) or upon a rise in intra-abdominal pressure due to filling of the urinary bladder, the device allows the user to provide conscious control to the device by voluntary action of the pelvic floor muscles, thus providing means for strengthening these muscles and providing rehabilitation for a woman suffering from SUI.

It is one object of the present invention to provide an intra-vaginal device for controlling urinary incontinence, designed to be placed longitudinally in the vagina, wherein said device comprises:
 a. a deformable distal portion designed to be placed in the subvesical region of the vagina; said deformable distal portion is characterized by a deformable state and an un-deformable state;
 b. a deformable proximal portion designed to be placed in the suburethral portion of the vagina; said deformable proximal portion is characterized by a deformable state and an un-deformable state;
 c. at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state;
wherein upon predetermined amount of intra-vaginal pressure applied on said proximal portion, said deformation controlling mechanism is adapted to transform proximal portion from said un-deformable state to said deformable state such that pressure is applied on said urethra.

It is another object of the present invention to provide the device as defined above, wherein said activation of said proximal portion comprises a change at least one of its size, shape, orientation, and position.

It is another object of the present invention to provide the device as defined above, wherein said change in at least one of the size, shape, orientation, and position of said proximal portion is of sufficient magnitude to close the urethra.

It is another object of the present invention to provide the device as defined above, wherein said proximal portion is inflatable and in fluid contact with said reservoir.

It is another object of the present invention to provide the device as defined above, wherein said proximal portion comprises a movable portion, and further comprising a guide, such that said proximal portion is free to move along said guide when said distal portion is in its deflated state but not when said distal portion is in its inflated state.

It is another object of the present invention to provide the device as defined above, wherein at least one of the length and the width of said device may be altered and then fixed at the altered value prior to insertion of said device into the vagina.

It is another object of the present invention to provide the device as defined above, wherein said proximal portion is adapted to activated upon increase of the intra-vaginal pressure (which in term correlates to both intra-abdominal pressure and to contraction of the pelvic floor muscles), intra-abdominal, contraction of the pelvic floor muscles or any combination thereof above a threshold value.

It is another object of the present invention to provide the device as defined above, wherein said proximal portion is activated to at least a base level, and activated to a higher level upon increase of the intra-vaginal pressure (which in term correlates to both intra-abdominal pressure and to contraction of the pelvic floor muscles), intra-abdominal, contraction of the pelvic floor muscles or any combination thereof pressure above a threshold value.

It is another object of the present invention to provide the device as defined above, wherein said proximal portion is adapted to provide constant pressure over a predetermined portion of its area, and a variable pressure over the remainder of its area.

It is another object of the present invention to provide the device as defined above, wherein said proximal portion is adapted to provide at least one selected from a group consisting of constant pressure, variable pressure, non-continuous pressure, homogeneous, non-homogeneous pressure.

It is another object of the present invention to provide the device as defined above, wherein activation of said proximal portion induces backflow from the urethra to the urinary bladder.

It is another object of the present invention to provide the device as defined above, further comprising means for providing pulsed activation of said proximal portion.

It is another object of the present invention to provide the device as defined above, further comprising at least one pressure sensor adapted to measure the intra-vaginal pressure.

It is another object of the present invention to provide the device as defined above, further comprising a control mechanism in contact with said pressure sensor, said control mechanism adapted to activate said proximal portion when the intra-vaginal pressure exceeds a predetermined threshold value.

It is another object of the present invention to provide the device as defined above, wherein said predetermined threshold value is the urethral pressure.

It is another object of the present invention to provide the device as defined above, wherein the outer surface of said distal portion in contact with substantially the entire circumference of the vaginal wall.

It is another object of the present invention to provide the device as defined above, wherein the outer surface of said distal portion is in contact with the vaginal wall in a plurality of separate locations.

It is another object of the present invention to provide the device as defined above, wherein said proximal portion is shaped to at least partially surround the urethra.

It is another object of the present invention to provide the device as defined above, further comprising absorbent material.

It is another object of the present invention to provide the device as defined above, wherein said absorbent material is placed at one of the longitudinal ends of said device.

It is another object of the present invention to provide the device as defined above, wherein said absorbent material substantially completely surrounds said device.

It is another object of the present invention to provide the device as defined above, wherein said device is sealed within a biocompatible material.

The use of the device as defined above for treating urinary incontinence.

It is another object of the present invention to provide the device as defined above, additionally comprising a diaphragm adapted to sense vaginal pressure, intra-abdominal pressure, contraction of the pelvic floor muscles or any combination thereof and to apply pressure on said urethra.

It is another object of the present invention to provide the device as defined above, wherein said device is constructed from shape memory material selected from a group consisting of Nitinol; electro-active polymers or any combination thereof.

It is another object of the present invention to provide the device as defined above, wherein said diaphragm is made of shape memory material, electro-active polymers or any combination thereof.

It is another object of the present invention to provide the device as defined above, wherein said deformable distal portion and said deformable proximal portion are coupled by at least one hinge or transmission mechanism.

It is another object of the present invention to provide the device as defined above, wherein inward displacement of said deformable distal portion results in and outward displacement of said deformable proximal portion.

It is another object of the present invention to provide the device as defined above, wherein said device is shaped as multi-directional clothes peg.

It is another object of the present invention to provide the device as defined above, wherein said deformable state and said un-deformable state of either said deformable distal portion or said deformable proximal portion is obtained by a change in said deformable distal portion or said deformable proximal portion; said change is selected from a group consisting of size, shape, orientation, and position and any combination thereof.

It is another object of the present invention to provide the device as defined above, wherein said deformable distal portion or said deformable proximal portion are rigid part-hinge-rigid parts.

It is another object of the present invention to provide the device as defined above, wherein said deformation controlling mechanism is unilateral valve.

It is another object of the present invention to provide the device as defined above, wherein said valve is characterized by at least two configurations; an open configuration, in which the same enables said reversible transformation of said distal portion or said proximal portion from said deformable state to said un-deformable state; and from said un-deformable state to said deformable state; and a closed configuration in which the same prevents said deformation.

It is another object of the present invention to provide the device as defined above, wherein said valve is preset to be in either said closed configuration and/or said open configuration for a predetermined amount of time.

It is another object of the present invention to provide the device as defined above, wherein said valve is self operated.

It is another object of the present invention to provide the device as defined above, wherein said valve is externally operated such that the reconfiguration from said open configuration to said close configuration and vice versa is activated by an external stimulus.

It is another object of the present invention to provide the device as defined above, wherein said external stimulus is selected from a group consisting of magnetic force, electrical stimulus, electromagnetic stimulus and any combination thereof.

It is another object of the present invention to provide the device as defined above, wherein said magnetic force is obtained by at least one magnet reversible coupled to the underwear of the patient.

It is another object of the present invention to provide the device as defined above, wherein said valve is operated electrically using a remote control.

It is another object of the present invention to provide an intra-vaginal device for controlling urinary incontinence, designed to be placed longitudinally in the vagina, wherein said device comprises:

a. an inflatable distal portion designed to be placed in the subvesical region of the vagina, said distal portion in fluid contact with a reservoir constructed of a material that is essentially non-deformable under pressure; and, a proximal portion designed to be placed in the suburethral portion of the vagina, said proximal portion in physical contact with said reservoir; wherein said distal portion is in its inflated state and adapted to be activated upon deflation of said distal portion.

It is another object of the present invention to provide the device as defined above, wherein said proximal portion, in its activated stage, is adapted to apply pressure on the urethra, such that urinary incontinence is treated.

It is another object of the present invention to provide the device as defined above, wherein said activation of said proximal portion comprises a change at least one of its size, shape, orientation, and position.

It is another object of the present invention to provide the device as defined above, wherein said proximal portion is adapted to provide at least one selected from a group consisting of constant pressure, variable pressure, non-continuous pressure, homogeneous, non-homogeneous pressure.

It is another object of the present invention to provide the device as defined above, wherein said change in at least one of the size, shape, orientation, and position of said proximal portion is of sufficient magnitude to close the urethra.

It is another object of the present invention to provide the device as defined above, wherein said proximal portion is inflatable and in fluid contact with said reservoir.

It is another object of the present invention to provide the device as defined above, further comprising a piston within said reservoir.

It is another object of the present invention to provide the device as defined above, wherein said reservoir is cantilevered to said distal portion.

It is another object of the present invention to provide the device as defined above, wherein said proximal portion comprises a movable portion, and further comprising a guide, such that said proximal portion is free to move along said guide when said distal portion is in its deflated state but not when said distal portion is in its inflated state.

It is another object of the present invention to provide the device as defined above, wherein at least one of the length and the width of said reservoir may be altered and then fixed at the altered value prior to insertion of said device into the vagina.

It is another object of the present invention to provide the device as defined above, wherein said proximal portion is adapted to activated upon increase of the intra-vaginal pressure (which in term correlates to both intra-abdominal pressure and to contraction of the pelvic floor muscles), intra-abdominal, contraction of the pelvic floor muscles or any combination thereof above a threshold value.

It is another object of the present invention to provide the device as defined above, wherein said proximal portion is activated to at least a base level, and activated to a higher level upon increase of the intra-vaginal pressure (which in term correlates to both intra-abdominal pressure and to contraction of the pelvic floor muscles), intra-abdominal, contraction of the pelvic floor muscles or any combination thereof above a threshold value.

It is another object of the present invention to provide the device as defined above, wherein said proximal portion is adapted to provide constant pressure over a predetermined portion of its area, and a variable pressure over the remainder of its area.

It is another object of the present invention to provide the device as defined above, wherein activation of said proximal portion induces backflow from the urethra to the urinary bladder.

It is another object of the present invention to provide the device as defined above, further comprising means for providing pulsed activation of said proximal portion.

It is another object of the present invention to provide the device as defined above, further comprising at least one pressure sensor adapted to measure the intra-vaginal pressure.

It is another object of the present invention to provide the device as defined above, further comprising a control mechanism in contact with said pressure sensor, said control mechanism adapted to activate said proximal portion when the intra-vaginal pressure (which in term correlates to both intra-abdominal pressure and to contraction of the pelvic floor muscles), intra-abdominal, contraction of the pelvic floor muscles or any combination thereof exceeds a predetermined threshold value.

It is another object of the present invention to provide the device as defined above, wherein said predetermined threshold value is the urethral pressure.

It is another object of the present invention to provide the device as defined above, wherein the outer surface of said distal portion in contact with substantially the entire circumference of the vaginal wall. It is another object of the present invention to provide the device as defined above, wherein the outer surface of said distal portion is in contact with the vaginal wall in a plurality of separate locations.

It is another object of the present invention to provide the device as defined above, wherein said proximal portion is shaped to at least partially surround the urethra.

It is another object of the present invention to provide the device as defined above, further comprising absorbent material.

It is another object of the present invention to provide the device as defined above, wherein said absorbent material is placed at one of the longitudinal ends of said device.

It is another object of the present invention to provide the device as defined above, wherein said absorbent material substantially completely surrounds said device.

It is another object of the present invention to provide the device as defined above, wherein said device is sealed within a biocompatible material.

It is another object of the present invention to provide the use of the device as defined above for treating urinary incontinence.

It is another object of the present invention to provide the device as defined above, configured as tampon.

It is another object of the present invention to provide the use of the device as defined above for rehabilitation of stress urinary incontinence by strengthening the pelvic muscles.

It is another object of the present invention to provide the use of the device as defined above for rehabilitation of stress urinary incontinence by strengthening the pelvic muscles.

It is another object of the present invention to provide the device as defined above, adapted to be activated upon organ prolapse.

It is another object of the present invention to provide the device as defined above, wherein said biofeedback mechanism is adapted to exercise the pelvic floor muscles.

It is another object of the present invention to provide the device as defined above, wherein said device is activated or said deformable distal or proximal portion are activated upon contraction of pelvic floor muscle such that said pelvic floor muscle are strengthened.

It is another object of the present invention to provide the device as defined above, wherein said device is constructed from shape memory material selected from a group consisting of Nitinol; electro-active polymers or any combination thereof.

It is another object of the present invention to provide the device as defined above, additionally comprising a diaphragm adapted sense-vaginal pressure, intra-abdominal, contraction of the pelvic floor muscles or any combination thereof and to apply pressure on said urethra.

It is another object of the present invention to provide the device as defined above, wherein said diaphragm is made of shape memory material, electro-active polymers or any combination thereof.

It is another object of the present invention to provide the device as defined above, wherein said deformable distal portion and said deformable proximal portion are coupled by at least one hinge or transmission mechanism.

It is another object of the present invention to provide the device as defined above, wherein inward displacement of said deformable distal portion results in and outward displacement of said deformable proximal portion.

It is another object of the present invention to provide the device as defined above, wherein said device is shaped as multi-directional clothes peg.

It is another object of the present invention to provide the device as defined above, wherein said deformable state and said un-deformable state of either said deformable distal portion or said deformable proximal portion is obtained by a change in said deformable distal portion or said deformable proximal portion; said change is selected from a group consisting of size, shape, orientation, and position and any combination thereof.

It is another object of the present invention to provide the device as defined above, additionally comprising a deformation controlling mechanism.

It is another object of the present invention to provide the device as defined above, wherein said deformation controlling mechanism is unilateral valve.

It is another object of the present invention to provide the device as defined above, wherein said valve is characterized by at least two configurations; an open configuration, in which the same enables said reversible transformation of said distal portion or said proximal portion from said deformable state to said un-deformable state; and from said un-deformable state to said deformable state; and a closed configuration in which the same prevents said deformation.

It is another object of the present invention to provide the device as defined above, wherein said valve is preset to be in either said closed configuration and/or said open configuration for a predetermined amount of time.

It is another object of the present invention to provide the device as defined above, wherein said valve is self operated.

It is another object of the present invention to provide the device as defined above, wherein said valve is externally operated such that the reconfiguration from said open configuration to said close configuration and vice versa is activated by an external stimulus.

It is another object of the present invention to provide the device as defined above, wherein said external stimulus is selected from a group consisting of magnetic force, electrical stimulus, electromagnetic stimulus and any combination thereof.

It is another object of the present invention to provide the device as defined above, wherein said magnetic force is obtained by at least one magnet reversible coupled to the underwear of the patient.

It is another object of the present invention to provide the device as defined above, wherein said valve is operated electrically using a remote control.

It is another object of the present invention to provide a method of treating urinary incontinence, comprising steps of
  a. providing an intra-vaginal device for controlling urinary incontinence, said device comprises;
    i. a deformable distal portion designed to be placed in the subvesical region of the vagina; said deformable distal portion is characterized by a deformable state and an un-deformable state;
    ii. a deformable proximal portion designed to be placed in the suburethral portion of the vagina; said deformable proximal portion is characterized by a deformable state and an un-deformable state;
    iii. at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state;
  b. inserting said device into the vagina such that said distal portion is located in the subvesical region and said proximal portion is located in the suburethral region; and,
  c. sensing intra-vaginal pressure;
  d. if said pressure is above predetermined threshold, said proximal portion of said device is activated, thereby applying pressure on the urethra such that urinary incontinence is treated.

It is another object of the present invention to provide a method of treating urinary incontinence, comprising steps of
  a. providing an intra-vaginal device for controlling urinary incontinence, said device comprises;
    i. an inflatable distal portion designed to be placed in the subvesical region of the vagina, said distal portion in fluid contact with a reservoir constructed of a material that is essentially non-deformable under pressure; and,
    ii. a proximal portion designed to be placed in the suburethral portion of the vagina, said proximal portion in physical contact with said reservoir; wherein said distal portion is in its inflated state and adapted to be activated upon deflation of said distal portion;
  b. inserting said device into the vagina such that said distal portion is located in the subvesical region and said proximal portion is located in the suburethral region; and,
  c. sensing intra-vaginal pressure;
  d. if said pressure is above predetermined threshold, said device is activated, thereby applying pressure on the urethra such that urinary incontinence is treated.

It is another object of the present invention to provide the methods as defined above, wherein said step of activation of said device further comprising step of activating said proximal portion.

It is another object of the present invention to provide the methods as defined above, wherein said step of activation additionally comprising step of changing at least one of its size, shape, orientation, and position.

It is another object of the present invention to provide the methods as defined above, wherein said change is in at least one of the size, shape, orientation, and position of said proximal portion is of sufficient magnitude to close the urethra.

It is another object of the present invention to provide the methods as defined above, wherein said proximal portion is inflatable and in fluid contact with said reservoir.

It is another object of the present invention to provide the methods as defined above, further comprising step of providing said reservoir with a piston within the same.

It is another object of the present invention to provide the methods as defined above, additionally comprising step of cantilevering said reservoir to said distal portion.

It is another object of the present invention to provide the methods as defined above, additionally comprising step of providing said proximal with a movable portion, and further comprising a guide, such that said proximal portion is free to move along said guide when said distal portion is in its deflated state but not when said distal portion is in its inflated state.

It is another object of the present invention to provide the methods as defined above, additionally comprising step of providing said device wherein at least one of the length and the width of said reservoir may be altered and then fixed at the altered value prior to insertion of said device into the vagina.

It is another object of the present invention to provide the methods as defined above, additionally comprising step of providing said device wherein at least one of the length and the width of said device may be altered and then fixed at the altered value prior to insertion of said device into the vagina.

It is another object of the present invention to provide the methods as defined above, additionally comprising step of activating said proximal portion upon increase of the intra-vaginal pressure (which in term correlates to both intra-abdominal pressure and to contraction of the pelvic floor muscles), intra-abdominal, contraction of the pelvic floor muscles or any combination thereof above a threshold value.

It is another object of the present invention to provide the methods as defined above, additionally comprising step of activating said proximal portion to at least a base level, and activated to a higher level upon increase of the intra-vaginal pressure (which in term correlates to both intra-abdominal pressure and to contraction of the pelvic floor muscles), intra-abdominal, contraction of the pelvic floor muscles or any combination thereof pressure above a threshold value.

It is another object of the present invention to provide the methods as defined above, additionally comprising step of providing constant pressure over a predetermined portion of its area, and a variable pressure over the remainder of its area by said proximal portion.

It is another object of the present invention to provide the methods as defined above, additionally comprising step of providing, by said proximal portion, at least one selected from a group consisting of constant pressure, variable pressure, non-continuous pressure, homogeneous, non-homogeneous pressure.

It is another object of the present invention to provide the methods as defined above, wherein activation of said proximal portion induces backflow from the urethra to the urinary bladder.

It is another object of the present invention to provide the methods as defined above, further comprising step of providing pulsed activation of said proximal portion.

It is another object of the present invention to provide the methods as defined above, further comprising step of measuring the intra-vaginal pressure (which in term correlates to both intra-abdominal pressure and to contraction of the pelvic floor muscles), intra-abdominal, contraction of the pelvic floor muscles or any combination thereof by at least one pressure sensor.

It is another object of the present invention to provide the methods as defined above, further comprising a control mechanism in contact with said pressure sensor, said control mechanism adapted to activate said proximal portion when the intra-vaginal pressure (which in term correlates to both intra-abdominal pressure and to contraction of the pelvic floor muscles), intra-abdominal, contraction of the pelvic floor muscles or any combination thereof exceeds a predetermined threshold value.

It is another object of the present invention to provide the methods as defined above, wherein said predetermined threshold value is the urethral pressure.

It is another object of the present invention to provide the methods as defined above, additionally comprising step of contacting the outer surface of said distal portion with substantially the entire circumference of the vaginal wall.

It is another object of the present invention to provide the methods as defined above, additionally comprising step of contacting the outer surface of said distal portion with the vaginal wall in a plurality of separate locations.

It is another object of the present invention to provide the methods as defined above, additionally comprising step of shaping said proximal portion to at least partially surround the urethra.

It is another object of the present invention to provide the methods as defined above, additionally comprising step of providing said device with an absorbent material.

It is another object of the present invention to provide the methods as defined above, additionally comprising step of placing said absorbent material at one of the longitudinal ends of said device.

It is another object of the present invention to provide the methods as defined above, additionally comprising step of completely surrounding said device with said absorbent material substantially.

It is another object of the present invention to provide the methods as defined above, additionally comprising step of sealing said device with a biocompatible material.

It is another object of the present invention to provide the methods as defined above, additionally comprising step of configuring said device as a tampon.

It is another object of the present invention to provide the methods as defined above, additionally comprising step of constructing said device from shape memory material selected from a group consisting of Nitinol; electro-active polymers or any combination thereof.

It is another object of the present invention to provide the methods as defined above, additionally comprising step of providing said device with at least one diaphragm adapted to sense vaginal pressure, intra-abdominal pressure, contraction of the pelvic floor muscles or any combination thereof and to apply pressure on said urethra.

It is another object of the present invention to provide the methods as defined above, additionally comprising step of constructing said diaphragm of shape memory material, electro-active polymers or any combination thereof.

It is another object of the present invention to provide the methods as defined above, wherein said deformable distal portion and said deformable proximal portion are coupled by at least one hinge or transmission mechanism.

It is another object of the present invention to provide the methods as defined above, wherein inward displacement of said deformable distal portion results in and outward displacement of said deformable proximal portion.

It is another object of the present invention to provide the methods as defined above, wherein said device is shaped as multi-directional clothes peg.

It is another object of the present invention to provide the methods as defined above, wherein said deformable state and said un-deformable state of either said deformable distal portion or said deformable proximal portion is obtained by a change in said deformable distal portion or said deformable proximal portion; said change is selected from a group consisting of size, shape, orientation, and position and any combination thereof.

It is another object of the present invention to provide the methods as defined above, wherein said deformable distal portion or said deformable proximal portion are rigid part-hinge-rigid parts.

It is another object of the present invention to provide the methods as defined above, wherein said deformation controlling mechanism is unilateral valve.

It is another object of the present invention to provide the methods as defined above, wherein said valve is characterized by at least two configurations; an open configuration, in which the same enables said reversible transformation of said distal portion or said proximal portion from said deformable state to said un-deformable state; and from said un-deformable state to said deformable state; and a closed configuration in which the same prevents said deformation.

It is another object of the present invention to provide the methods as defined above, additionally comprising step of presetting said valve to be in either said closed configuration and/or said open configuration for a predetermined amount of time.

It is another object of the present invention to provide the methods as defined above, wherein said valve is self operated.

It is another object of the present invention to provide the methods as defined above, additionally comprising step of externally operating said valve such that the reconfiguration from said open configuration to said close configuration and vice versa is activated by an external stimulus.

It is another object of the present invention to provide the methods as defined above, wherein said external stimulus is selected from a group consisting of magnetic force, electrical stimulus, electromagnetic stimulus and any combination thereof.

It is another object of the present invention to provide the methods as defined above, wherein said magnetic force is obtained by at least one magnet reversible coupled to the underwear of the patient.

It is another object of the present invention to provide the methods as defined above, wherein said valve is operated electrically using a remote control.

It is another object of the present invention to provide the methods as defined above, wherein said device is shaped as multi-directional clothes peg.

It is another object of the present invention to provide the methods as defined above, wherein said deformable state and said un-deformable state of either said deformable distal portion or said deformable proximal portion is obtained by a change in said deformable distal portion or said deformable proximal portion; said change is selected from a group consisting of size, shape, orientation, and position and any combination thereof.

It is another object of the present invention to provide the methods as defined above, additionally comprising a deformation controlling mechanism.

It is another object of the present invention to provide the methods as defined above, wherein said deformation controlling mechanism is unilateral valve.

It is another object of the present invention to provide the methods as defined above, wherein said valve is characterized by at least two configurations; an open configuration, in which the same enables said reversible transformation of said distal portion or said proximal portion from said deformable state to said un-deformable state; and from said un-deformable state to said deformable state; and a closed configuration in which the same prevents said deformation.

It is another object of the present invention to provide the methods as defined above, additionally comprising step of presetting said valve to be in either said closed configuration and/or said open configuration for a predetermined amount of time.

It is another object of the present invention to provide the methods as defined above, wherein said valve is self operated.

It is another object of the present invention to provide the methods as defined above, additionally comprising step of externally operating said valve such that the reconfiguration from said open configuration to said close configuration and vice versa is activated by an external stimulus.

It is another object of the present invention to provide the methods as defined above, wherein said external stimulus is selected from a group consisting of magnetic force, electrical stimulus, electromagnetic stimulus and any combination thereof.

It is another object of the present invention to provide the methods as defined above, wherein said magnetic force is obtained by at least one magnet reversible coupled to the underwear of the patient.

It is another object of the present invention to provide the methods as defined above, wherein said valve is operated electrically using a remote control.

It is another object of the present invention to provide a method for rehabilitation of stress urinary incontinence, comprising:
a. obtaining an intra-vaginal device for controlling urinary incontinence;
b. inserting said device into the vagina such that said distal portion is located in the subvesical region and said proximal portion is located in the suburethral region; and,
c. contracting at least a portion of the pelvic muscles, whereby said proximal portion closes said urethra;
wherein said pelvic muscles are strengthened.

It is another object of the present invention to provide the methods as defined above, further including a step of holding said pelvic muscles in their contracted position for a predetermined length of time.

It is another object of the present invention to provide the methods as defined above, wherein said step of providing a obtaining an intra-vaginal device for controlling urinary incontinence additionally comprising step of providing said device with: (a) a deformable distal portion designed to be placed in the subvesical region of the vagina; said deformable distal portion is characterized by a deformable state and an un-deformable state; (b) a deformable proximal portion designed to be placed in the suburethral portion of the vagina; said deformable proximal portion is characterized by a deformable state and an un-deformable state; (c) at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state.

It is another object of the present invention to provide the methods as defined above, wherein said step of providing a obtaining an intra-vaginal device for controlling urinary incontinence additionally comprising step of providing said device with: (a) an inflatable distal portion designed to be placed in the subvesical region of the vagina, said distal portion in fluid contact with a reservoir constructed of a material that is essentially non-deformable under pressure; and, (b) a proximal portion designed to be placed in the suburethral portion of the vagina, said proximal portion in physical contact with said reservoir; wherein said distal portion is in its inflated state and adapted to be activated upon deflation of said distal portion.

It is another object of the present invention to provide the methods as defined above, additionally comprising step of constructing said device is from shape memory material selected from a group consisting of Nitinol; electro-active polymers or any combination thereof.

It is another object of the present invention to provide the methods as defined above, additionally comprising step of providing said device with at least one diaphragm adapted sense-vaginal pressure, intra-abdominal, contraction of the pelvic floor muscles or any combination thereof and to apply pressure on said urethra.

It is another object of the present invention to provide the methods as defined above, additionally comprising step of constructing said diaphragm of shape memory material, electro-active polymers or any combination thereof.

It is still an object of the present invention to provide the methods as defined above, additionally comprising step of configuring said device as a tampon.

It is still an object of the present invention to provide the methods as defined above, for treating at least one selected from a group consisting of menstrual pain, interstitial cystitis, pelvic pain, chronic pelvic pain, painful bladder syndrome or any combination thereof.

It is still an object of the present invention to provide the device as defined above, for treating at least one selected from a group consisting of menstrual pain, interstitial cystitis, pelvic pain, chronic pelvic pain, painful bladder syndrome or any combination thereof.

BRIEF DESCRIPTION OF THE DRAWINGS

The invention is now described with reference to the drawings, in which.

DETAILED DESCRIPTION OF THE PREFERRED EMBODIMENTS

Figure 1:
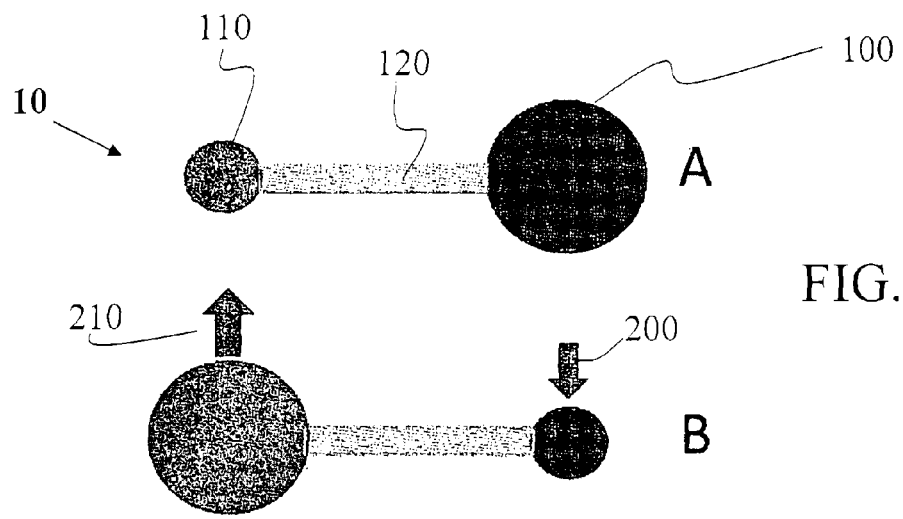
FIG. 1 shows a schematic diagram of the action of one embodiment of the invention herein disclosed.

The present invention is described hereinafter with reference to the drawings and examples, in which preferred embodiments are described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

The invention herein disclosed is designed to meet these needs. The device comprises a dynamic mechanism that keeps a baseline pressure that is increased upon triggering by a rise in the intra-vaginal pressure (which in term is correlated to both intra-abdominal pressure and to contraction of the pelvic floor muscles), intra-abdominal, contraction of the pelvic floor muscles or any combination thereof.

The device of the present invention is operated both involuntary after a rise in intraabdominal pressure or by voluntary control through pelvic floor muscle contraction.

The present invention provides an intra-vaginal device for controlling urinary incontinence, designed to be placed longitudinally in the vagina, wherein said device comprises:
  a. a deformable distal portion designed to be placed in the subvesical region of the vagina; said deformable distal portion is characterized by a deformable state and an un-deformable state;
  b. a deformable proximal portion designed to be placed in the suburethral portion of the vagina; said deformable proximal portion is characterized by a deformable state and an un-deformable state;
  c. at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state;
wherein upon predetermined amount of intra-vaginal pressure applied on said proximal pressure, said deformation controlling mechanism is adapted to transform proximal portion from said un-deformable state to said deformable state such that pressure is applied on said urethra.

It should be emphasized that the deformation controlling mechanism acts as force transmitting means. Namely, when force is applied on either one of the distal or proximal portion the mechanism is adapted to 'transmit' the force to the other side. Hence when predetermined amount of pressure is sensed (of the intra-vaginal pressure) on the distal portion, the mechanism is adapted to transform the proximal portion from it un-deformed configuration to its deformed configuration so as to apply pressure on the urethra.

By applying pressure on the urethra, urinary incontinence is forceless (at least partially close) or prevented.

The present also provides an intra-vaginal device for controlling urinary incontinence, designed to be placed longitudinally in the vagina, wherein said device comprises:
  a. an inflatable distal portion designed to be placed in the subvesical region of the vagina, said distal portion in fluid contact with a reservoir constructed of a material that is essentially non-deformable under pressure; and,
  b. a proximal portion designed to be placed in the suburethral portion of the vagina, said proximal portion in physical contact with said reservoir; wherein said proximal portion is in its inflated state and adapted to be activated upon deflation of said distal portion.

The term "subvescial" refers hereinafter to the area extending from the uretro-vesical junction (i.e. the beginning of the urethra) to the cervix.

The term "suburethral" refers hereinafter to the area extending from the uretro-vesical junction (i.e. the beginning of the urethra) to the urethral orifice (i.e. vaginal opening to the bodies surface).

The term "threshold value" refers hereinafter to any value ranging from 1 mmhg to 80 about mmhg.

The term "about" refers hereinafter to a range of 25% below or above the referred value.

The term "Electroactive Polymers" or "EAPs", refers hereinafter to polymers that exhibits a change in size or shape when stimulated by an electric field.

Reference is now made to FIG. 1, which shows a schematic diagram of the principles of one preferred embodiment 10 of the invention herein disclosed. The device comprises an inflatable distal portion 100 and a proximal portion 110. The inflatable distal portion is in fluid connection with a reservoir 120, and at least during the time that the distal portion is inflated, the proximal portion is in contact with the reservoir as well. The reservoir is made of stiff material (preferably a hard biocompatible plastic) that is substantially non-deformable under pressure, i.e. it will not deform significantly at typical intra-vaginal pressure, intraabdominal, contraction of the pelvic floor muscles or any combination thereof. In the specific embodiment illustrated in FIG. 1, the distal portion is also inflatable and in fluid contact with the reservoir; the entire apparatus is sealed so that no external source or reservoir for the gas within it is necessary for its use. FIG. 1A shows the device with the distal portion inflated and the proximal portion substantially deflated. FIG. 1B illustrates the behavior of the device upon application of pressure 200 to the distal portion. The pressure will cause the distal portion to at least partially deflate. Since the inflatable proximal portion is in fluid contact with the distal portion, the pressure within the proximal portion will increase, causing it to at least partially inflate 210.

Figure 2A:
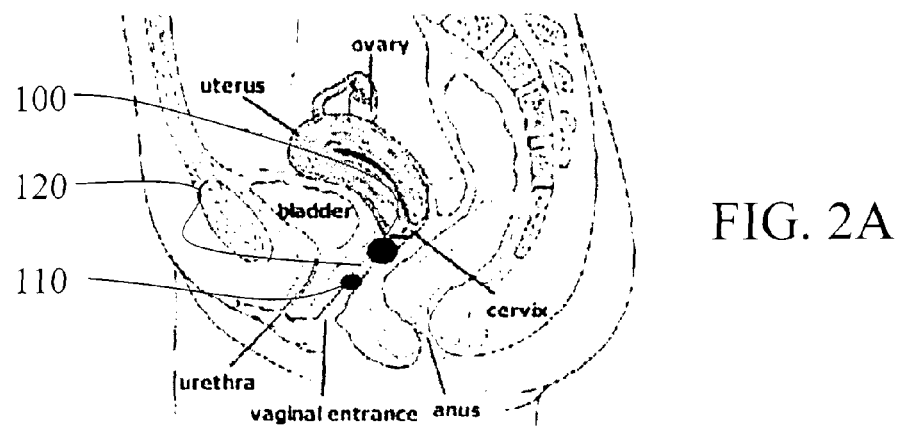
FIG. 2 shows a schematic diagram of one embodiment of the invention herein disclosed as it is used in practice.

Reference is now made to FIG. 2, which illustrates a typical use of embodiment 10 of the invention. As shown in FIG. 2A, the device is inserted into the vaginal cavity such that distal portion 100 is located in the subvesical region of the vagina and proximal portion 110 of the device is located in the suburethral region of the vagina. In preferred embodiments, the external surface of the distal portion is in contact with substantially the entire inner circumference of the vagina. In other embodiments, the external surface of the distal portion is shaped such that it only contacts certain areas of the internal circumference of the vagina.

Figure 2B:
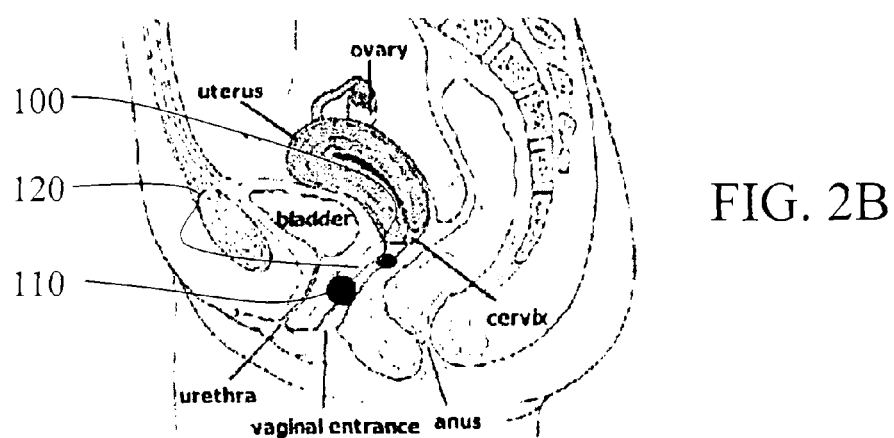

Reference is now made to FIG. 2B, which shows the action of the device upon an increase of intra-vaginal pressure, intra-abdominal, contraction of the pelvic floor muscles or any combination thereof. As can be seen from the figure, the placement of the device is such that this increase can be due to filling of the urinary bladder, or due to body motions such as coughing, sneezing, etc. The increase of the intra-vaginal pressure, intra-abdominal, contraction of the pelvic floor muscles or any combination thereof squeezes distal portion 100, which causes it to at least partially deflate, thus causing proximal portion 110 to at least partially inflate.

The inflation of the proximal portion thus results in the application of pressure on the urethra that eventually promotes urinary continence.

According to one embodiment the application of pressures causes the urethra to close, thus, preventing passage of urine. Upon relaxation of the intra-vaginal pressure, intraabdominal, contraction of the pelvic floor muscles or any combination thereof, the device returns to its original state. Thus, the device exerts pressure on the urethra only during the time that such pressure is necessary to prevent incontinence, lessening the likelihood of tissue damage due to pressure on the urethra.

In the simplest possible case shown in FIGS. 1 and 2, the proximal portion is spherical or ellipsoidal in shape. In preferred embodiments, it is shaped to at least partially surround or encompass the urethra. As a non-limiting example, it can comprise two "legs" each of which sits on one side of the urethra. In other embodiments, it may be "U" or "Y" shaped such that the urethra sits in the interior of the "U" or "Y." Inflation of the proximal portion thus squeezes the urethra from the bottom and sides. According to one embodiment said squeezing lowers the total pressure needed to close the urethra.

In still other embodiments of the invention, pressure on the distal portion can activate the proximal portion by other changes, such as changes in size, shape, or orientation such that the changed size, shape or orientation applies pressure on the urethra. The device, for example, may include a piston within the reservoir. Deflation of the distal portion causes the piston to move toward the proximal portion, where it can activate a change in size by inflating the proximal portion, a change in orientation by driving a screw in physical connection with the proximal portion, causing the proximal portion to turn, etc.

In still other embodiments of the invention, the reservoir is cantilevered with respect to the distal portion. In these embodiments, a change in intra-vaginal pressure, intraabdominal, contraction of the pelvic floor muscles or any combination thereof will cause the deflating distal portion to change the angle at which the reservoir sits relative to the wall of the distal portion and consequently with respect to the vaginal wall as well. This motion will bring the proximal portion into closer contact with the urethra, increasing the pressure on the urethra and closing it.

Because the unit is self-contained, it can be produced as a "one size fits all" device. In preferred embodiments, the reservoir is designed such that it can be lengthened or shortened to the length appropriate to the body of a specific user and then locked prior to insertion. Many methods for this are known in the art. For example, the reservoir can be provided in two portions that can rotate or slide relative to one another and with a tab or button to prevent further motion. The unit can also be designed such that its width is set to one that is appropriate to the specific user. This may be most easily done by varying the amount of gas within; at a given pressure, the more gas inside the inflatable section, the wider its diameter.

Different embodiments of the device may have different thresholds for activation. For example, the device may be designed such that activation of the proximal portion occurs only upon the intra-vaginal pressure, intra-abdominal, contraction of the pelvic floor muscles or any combination thereof exceeding a threshold value (in preferred embodiments, the threshold value is the urethral pressure). Alternatively, the proximal portion remains partially activated even when the intra-abdominal pressure is at its baseline value, and is activated to a higher level (e.g. sufficient to close the urethra entirely) only when the intra-vaginal pressure, intra-abdominal, contraction of the pelvic floor muscles or any combination thereof exceeds a threshold value. The threshold value can be set by choosing materials of appropriate stiffness such that the extent of inflation and deflation of the proximal and distal portions of the device are appropriate for the desired pressure. Alternatively, the device can include one or more pressure sensors. These pressure sensors can be connected to activation means that are programmed to activate the proximal portion to a predetermined extent depending on the intra-vaginal pressure, intra-abdominal, contraction of the pelvic floor muscles or any combination thereof. These activation means can, in various embodiments, induce the proximal portion to provide a constant pressure, or a pressure with a time-varying profile (e.g. ramped, stepped, or pulsed).

It is within the scope of the invention wherein the proximal portion produces a constant pressure over only part of its area, and a variable pressure over the remainder. This property can be achieved by making the proximal portion out of a plurality of materials of different stiffness, or with a shape that provides better contact (and hence higher pressure) in some places than in others.

In general, the proximal portion of the device will not be located at the point at which the urethra connects to the urinary bladder, so even when the device is activated, a small amount of urine is expected to escape from the urinary bladder into the urethra. When the activation ceases, this small amount of urine will then escape the body altogether. To prevent this from occurring, in preferred embodiments of the invention, the proximal portion is designed such that upon its activation, it induces backflow of urine into the urinary bladder.

In yet other embodiments of the invention, it further comprises absorbent material and thus acts as a tampon. The absorbent material can be placed at one or both of the longitudinal ends of the device, or can completely surround it. In yet other embodiments of the invention, it is sealed in a biocompatible material.

Figure 3A:
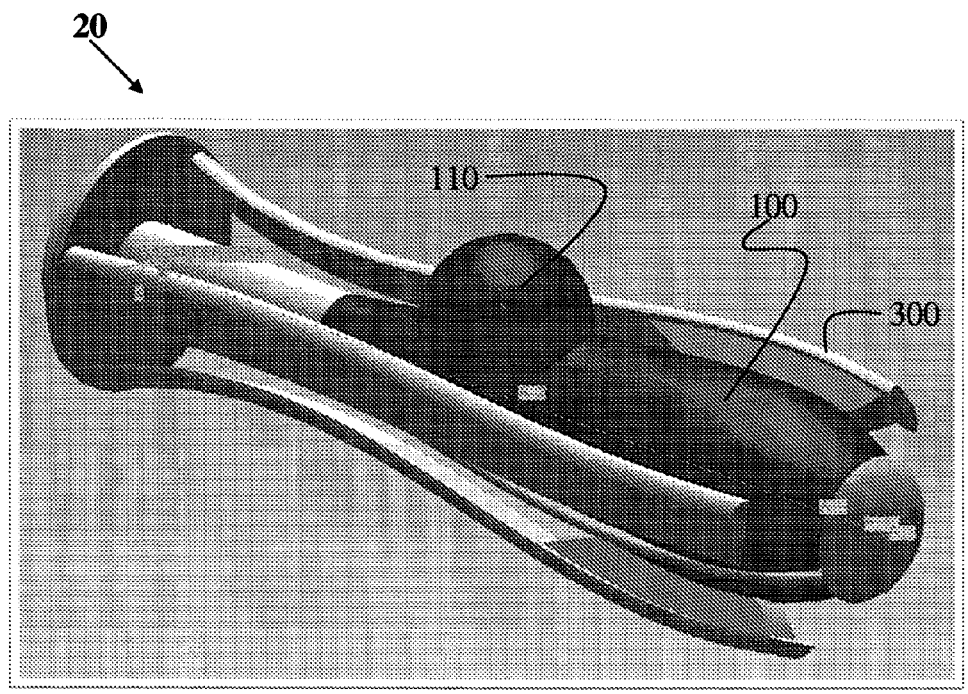
FIGS. 3-4 shows two views of another embodiment of the invention herein disclosed.
Figure 3B:
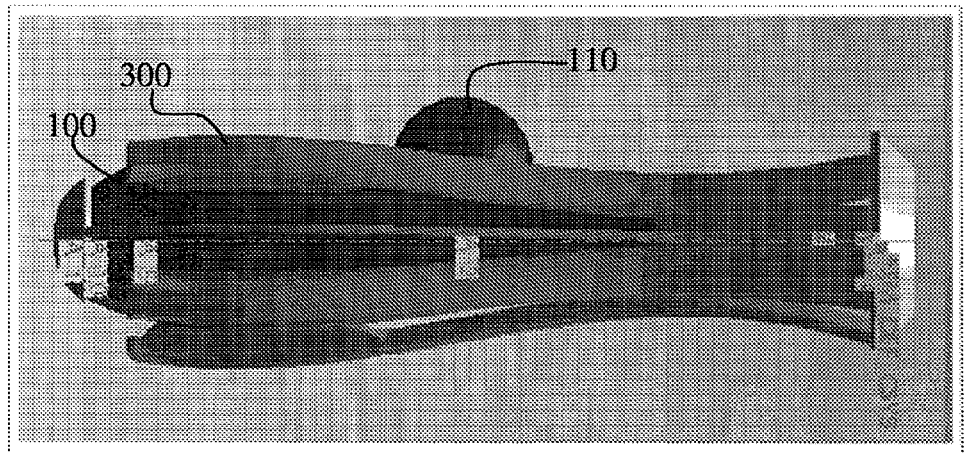

Reference is now made to FIGS. 3a and 3b, which presents two views of a second embodiment 20 of the device. In this embodiment, proximal portion 110 comprises a movable object such as a sphere as shown in the figure. The movement of the movable object constrained by a guide 300 that restricts the motion of the movable object to a certain direction and distance, and by the inflatable distal portion 100. When the distal portion is inflated, because of the constraints placed upon it by the guide, the proximal portion has no freedom of motion. When the intra-vaginal pressure, intra-abdominal, contraction of the pelvic floor muscles or any combination thereof increases, the distal portion at least partially deflates, freeing the movable portion to move within the guide. The proximal portion then moves to the side of the urethra, which closes due to contact with the proximal portion. It is also within the scope of the invention to disclose a method for treating urinary incontinence. The method comprises using the device as described in detail above.

It is also within the scope of the invention to disclose a method for rehabilitation of a female suffering from urinary incontinence. By this method, the device is placed within the vagina as described above. The individual then contracts the pelvic muscles, causing the distal portion to deflate at least partially, and the proximal portion to apply pressure on the urethra. This step can be repeated as often as the individual wishes. The method can also comprise contracting the pelvic muscles and keeping them contracted for a predetermined amount of time before relaxing them. This method has the net effect of strengthening the pelvic muscles and thus lessening or eliminating the individual's incontinence.

As mentioned above, the device of the present invention is operated both involuntary manner (after e.g., rise in intra-abdominal pressure) or by voluntary control through pelvic floor muscle contraction.

In the voluntary aspect of operation (pelvic floor muscles) the device is in fact a rehabilitator.

The rehabilitation device will offer rehabilitation through exercise of pelvic floor muscles.

In other words, the device is used as a biofeedback pelvic floor muscle exerciser.

As mentioned above, one of the benefits of having strong pelvic floor muscles is prevention and treatment of stress urinary incontinence other benefits are prevention and treatment of organ prolapse, better sexual health etc.

Thus, according to one embodiment of the present invention, the device additionally comprising a biofeedback mechanism adapted to be activated upon organ prolapse.

According to another embodiment, the biofeedback mechanism is adapted to exercise the pelvic floor muscles.

According to another embodiment, the device is activated (namely, said deformable distal or proximal portion are activated) upon contraction of pelvic floor muscle such that said pelvic floor muscle are strengthened.

It is one object of the present invention to provide an intra-vaginal device for controlling urinary incontinence, designed to be placed longitudinally in the vagina, wherein said device comprises:

a. a deformable distal portion designed to be placed in the subvesical region of the vagina; said deformable distal portion is characterized by a deformable state and an un-deformable state;

b. a deformable proximal portion designed to be placed in the suburethral portion of the vagina; said deformable proximal portion is characterized by a deformable state and an un-deformable state;

c. at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state;

wherein upon predetermined amount of intra-vaginal pressure applied on said proximal pressure, said deformation controlling mechanism is adapted to transform proximal portion from said un-deformable state to said deformable state such that pressure is applied on said urethra.

It is another object of the present invention to provide the device as defined above, wherein said activation of said proximal portion comprises a change at least one of its size, shape, orientation, and position.

It is another object of the present invention to provide the device as defined above, wherein said change in at least one of the size, shape, orientation, and position of said proximal portion is of sufficient magnitude to apply pressure on the urethra and at least partially close the same.

It is another object of the present invention to provide the device as defined above, wherein said proximal portion is inflatable and in fluid contact with said reservoir.

It is another object of the present invention to provide the device as defined above, wherein said proximal portion comprises a movable portion, and further comprising a guide, such that said proximal portion is free to move along said guide when said distal portion is in its deflated state but not when said distal portion is in its inflated state.

It is another object of the present invention to provide the device as defined above, wherein at least one of the length and the width of said device may be altered and then fixed at the altered value prior to insertion of said device into the vagina.

It is another object of the present invention to provide the device as defined above, wherein said proximal portion is adapted to activated upon increase of the intra-vaginal pressure, intra-abdominal, contraction of the pelvic floor muscles or any combination thereof above a threshold value.

It is another object of the present invention to provide the device as defined above, wherein said proximal portion is activated to at least a base level, and activated to a higher level upon increase of the intra-vaginal pressure, intra-abdominal, contraction of the pelvic floor muscles or any combination thereof above a threshold value.

It is another object of the present invention to provide the device as defined above, wherein said proximal portion is adapted to provide constant pressure over a predetermined portion of its area, and a variable pressure over the remainder of its area.

It is another object of the present invention to provide the device as defined above, wherein said proximal portion is adapted to provide at least one selected from a group consisting of constant pressure, variable pressure, non-continuous pressure, homogeneous, non-homogeneous pressure.

It is another object of the present invention to provide the device as defined above, wherein activation of said proximal portion induces backflow from the urethra to the urinary bladder.

It is another object of the present invention to provide the device as defined above, further comprising means for providing pulsed activation of said proximal portion.

It is another object of the present invention to provide the device as defined above, further comprising at least one pressure sensor adapted to measure the intra-vaginal pressure, intraabdominal, contraction of the pelvic floor muscles or any combination thereof.

It is another object of the present invention to provide the device as defined above, further comprising a control mechanism in contact with said pressure sensor, said control mechanism adapted to activate said proximal portion when the intra-vaginal pressure, intra-abdominal, contraction of the pelvic floor muscles or any combination thereof exceeds a predetermined threshold value.

It is another object of the present invention to provide the device as defined above, wherein said predetermined threshold value is the urethral pressure.

It is another object of the present invention to provide the device as defined above, wherein the outer surface of said distal portion in contact with substantially the entire circumference of the vaginal wall.

It is another object of the present invention to provide the device as defined above, wherein the outer surface of said distal portion is in contact with the vaginal wall in a plurality of separate locations.

It is another object of the present invention to provide the device as defined above, wherein said proximal portion is shaped to at least partially surround the urethra.

It is another object of the present invention to provide the device as defined above, further comprising absorbent material.

It is another object of the present invention to provide the device as defined above, wherein said absorbent material is placed at one of the longitudinal ends of said device.

It is another object of the present invention to provide the device as defined above, wherein said absorbent material substantially completely surrounds said device.

It is another object of the present invention to provide the device as defined above, wherein said device is sealed within a biocompatible material.

The use of the device as defined above for treating urinary incontinence.

It is another object of the present invention to provide the device as defined above, additionally comprising a diaphragm adapted sense-vaginal pressure, intra-abdominal, contraction of the pelvic floor muscles or any combination thereof and to apply pressure on said urethra.

It is another object of the present invention to provide the device as defined above, wherein said device is constructed from shape memory material selected from a group consisting of Nitinol; electro-active polymers or any combination thereof.

It is another object of the present invention to provide the device as defined above, wherein said diaphragm is made of shape memory material, electro-active polymers or any combination thereof.

It is another object of the present invention to provide an intra-vaginal device for controlling urinary incontinence, designed to be placed longitudinally in the vagina, wherein said device comprises:
  a. an inflatable distal portion designed to be placed in the subvesical region of the vagina, said distal portion in fluid contact with a reservoir constructed of a material that is essentially non-deformable under pressure; and,
  b. a proximal portion designed to be placed in the suburethral portion of the vagina, said proximal portion in physical contact with said reservoir; wherein said distal portion is in its inflated state and adapted to be activated upon deflation of said distal portion.

It is another object of the present invention to provide the device as defined above, wherein said proximal portion, in its activated stage, is adapted to apply pressure on the urethra, such that urinary incontinence is treated.

It is another object of the present invention to provide the device as defined above, wherein said activation of said proximal portion comprises a change at least one of its size, shape, orientation, and position.

It is another object of the present invention to provide the device as defined above, wherein said proximal portion is adapted to provide at least one selected from a group consisting of constant pressure, variable pressure, non-continuous pressure, homogeneous, non-homogeneous pressure.

It is another object of the present invention to provide the device as defined above, wherein said change in at least one of the size, shape, orientation, and position of said proximal portion is of sufficient magnitude to apply pressure on the urethra and at least partially close the same.

It is another object of the present invention to provide the device as defined above, wherein said proximal portion is inflatable and in fluid contact with said reservoir.

It is another object of the present invention to provide the device as defined above, further comprising a piston within said reservoir.

It is another object of the present invention to provide the device as defined above, wherein said reservoir is cantilevered to said distal portion.

It is another object of the present invention to provide the device as defined above, wherein said proximal portion comprises a movable portion, and further comprising a guide, such that said proximal portion is free to move along said guide when said distal portion is in its deflated state but not when said distal portion is in its inflated state.

It is another object of the present invention to provide the device as defined above, wherein at least one of the length and the width of said reservoir may be altered and then fixed at the altered value prior to insertion of said device into the vagina.

It is another object of the present invention to provide the device as defined above, wherein said proximal portion is adapted to activated upon increase of the intra-vaginal pressure, intra-abdominal, contraction of the pelvic floor muscles or any combination thereof above a threshold value.

It is another object of the present invention to provide the device as defined above, wherein said proximal portion is activated to at least a base level, and activated to a higher level upon increase of the intra-vaginal pressure, intra-abdominal, contraction of the pelvic floor muscles or any combination thereof above a threshold value.

It is another object of the present invention to provide the device as defined above, wherein said proximal portion is adapted to provide constant pressure over a predetermined portion of its area, and a variable pressure over the remainder of its area.

It is another object of the present invention to provide the device as defined above, wherein activation of said proximal portion induces backflow from the urethra to the urinary bladder.

It is another object of the present invention to provide the device as defined above, further comprising means for providing pulsed activation of said proximal portion.

It is another object of the present invention to provide the device as defined above, further comprising at least one pressure sensor adapted to measure the intra-vaginal pressure, intraabdominal, contraction of the pelvic floor muscles or any combination thereof.

It is another object of the present invention to provide the device as defined above, further comprising a control mechanism in contact with said pressure sensor, said control mechanism adapted to activate said proximal portion when the intra-vaginal pressure, intra-abdominal, contraction of the pelvic floor muscles or any combination thereof exceeds a predetermined threshold value.

It is another object of the present invention to provide the device as defined above, wherein said predetermined threshold value is the urethral pressure.

It is another object of the present invention to provide the device as defined above, wherein the outer surface of said distal portion in contact with substantially the entire circumference of the vaginal wall.

It is another object of the present invention to provide the device as defined above, wherein the outer surface of said distal portion is in contact with the vaginal wall in a plurality of separate locations.

It is another object of the present invention to provide the device as defined above, wherein said proximal portion is shaped to at least partially surround the urethra.

It is another object of the present invention to provide the device as defined above, further comprising absorbent material.

It is another object of the present invention to provide the device as defined above, wherein said absorbent material is placed at one of the longitudinal ends of said device.

It is another object of the present invention to provide the device as defined above, wherein said absorbent material substantially completely surrounds said device.

It is another object of the present invention to provide the device as defined above, wherein said device is sealed within a biocompatible material.

It is another object of the present invention to provide the use of the device as defined above for treating urinary incontinence.

It is another object of the present invention to provide the device as defined above, configured as tampon.

It is another object of the present invention to provide the use of the device as defined above for rehabilitation of stress urinary incontinence by strengthening the pelvic muscles.

It is another object of the present invention to provide the use of the device as defined above for rehabilitation of stress urinary incontinence by strengthening the pelvic muscles.

It is another object of the present invention to provide the device as defined above, wherein said device is constructed from shape memory material selected from a group consisting of Nitinol; electro-active polymers or any combination thereof.

It is another object of the present invention to provide the device as defined above, additionally comprising a diaphragm adapted sense-vaginal pressure, intra-abdominal, contraction of the pelvic floor muscles or any combination thereof and to apply pressure on said urethra.

It is emphasized that according to one embodiment, the shape memory invertible diaphragm is adapted to both absorb pressure and to exert pressure. The diaphragm has shape memory characteristics so that it "remembers" to go back to specific shape once the pressure exerted over it subsides.

Figure 4A:
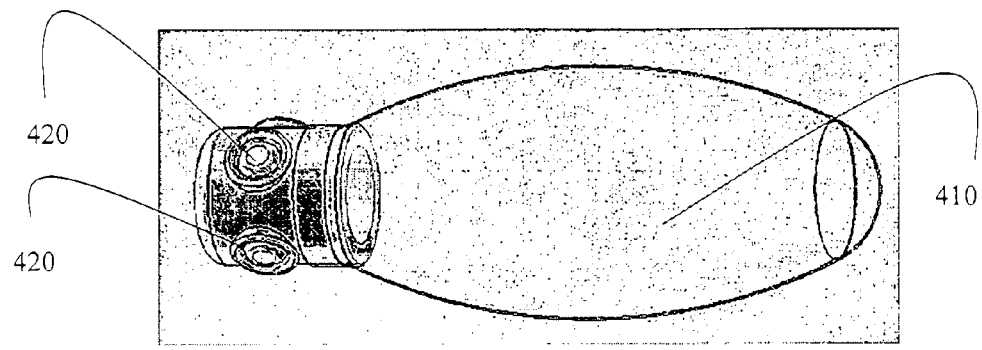
Figure 4B:
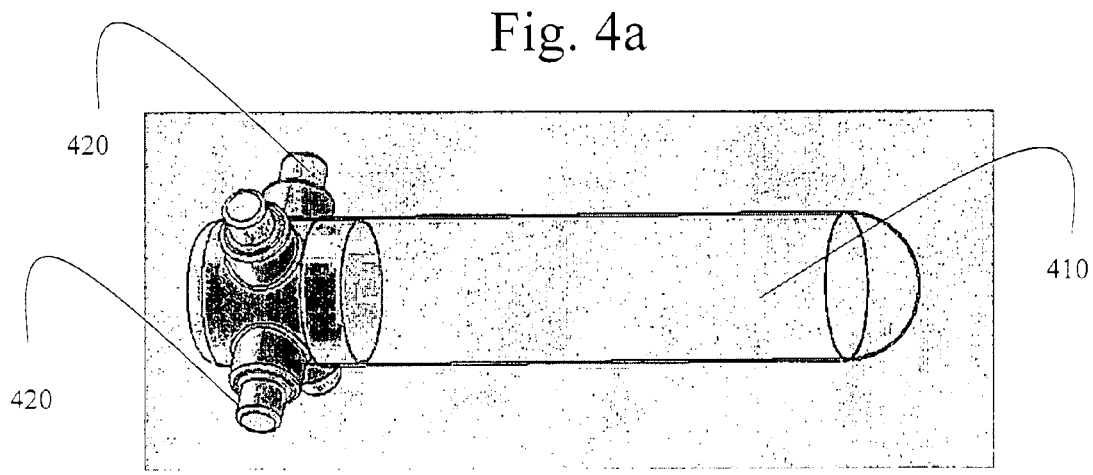

Reference is now made to FIGS. 4a and 4b, illustrating said embodiment of said diaphragm. As can be seen in FIG. 4a, the diaphragm 410 inflates (due to the intra-vaginal pressure, intra-abdominal, contraction of the pelvic floor muscles or any combination thereof increases) and thus, apply pressure.

According to another embodiment, seen in FIG. 4b, the application of pressure is obtained by a plurality of elements (numerical reference 420) protruding out.

Figure 4C:
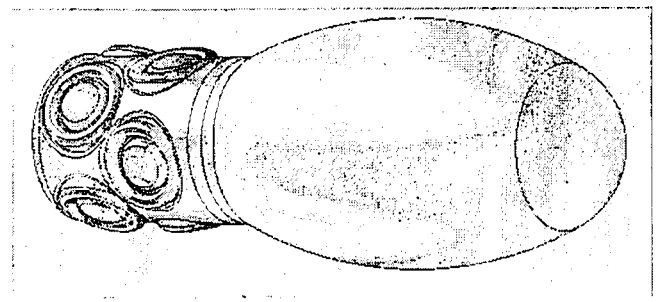

FIG. 4c illustrates the same.

It is another object of the present invention to provide the device as defined above, wherein said diaphragm is made of shape memory material, electro-active polymers or any combination thereof.

Figure 5A:
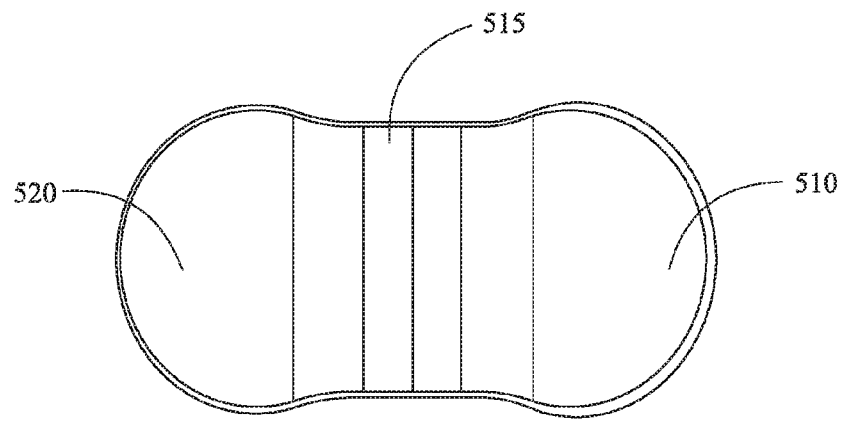
FIGS. 5a-5b illustrate another embodiment of the present invention, in which the device utilized changes in device material thickness to allow greater displacement of applying portion part.
Figure 5B:
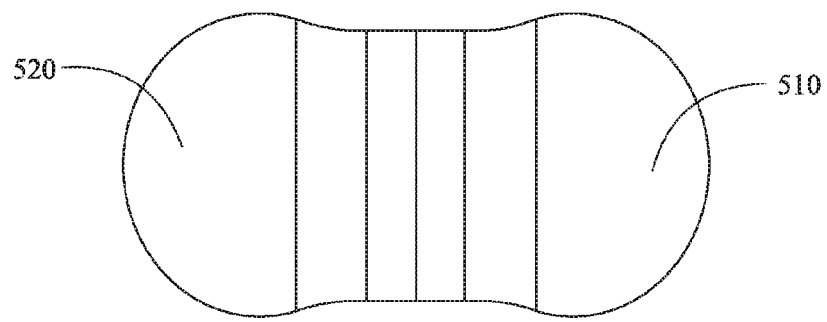

Reference is now made to FIGS. 5a-5b which illustrate another embodiment of the present invention, in which the device utilizes changes in the device's material thickness to allow greater displacement of applying portion part.

Portion 510 is receiving the intravaginal pressure and the portion 520 is exerting the pressure on the vaginal wall. Each portion is characterized by a different thickness. As can be seen portion 510 is characterized by a material having greater thickness than portion 520. Portion 520 is made of material having thinner material.

This design uses changes in device material thickness to allow greater displacement of portion 520.

Portion 510 and portion 520 are coupled together by a the bridging part 515 so as to couple the two different thicknesses.

FIG. 5b illustrates the same embodiment but from a side view.

Figure 6A:
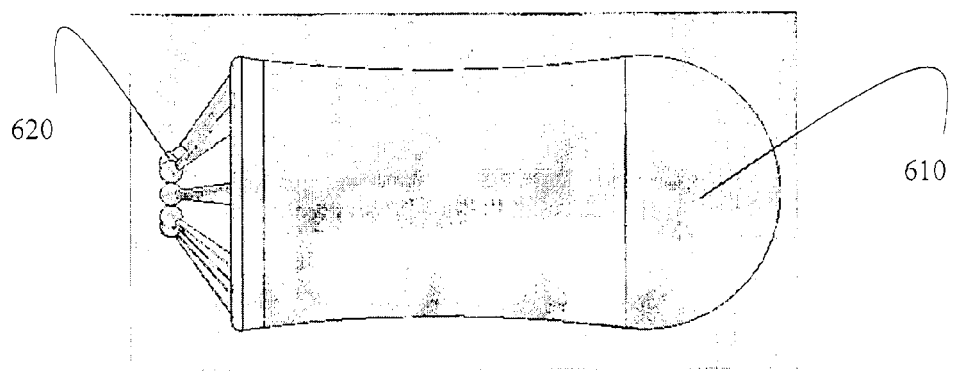
FIGS. 6a-6b illustrate a mechanism that is increasing its outer diameter with an increase in the pressure inside the device.
Figure 6B:
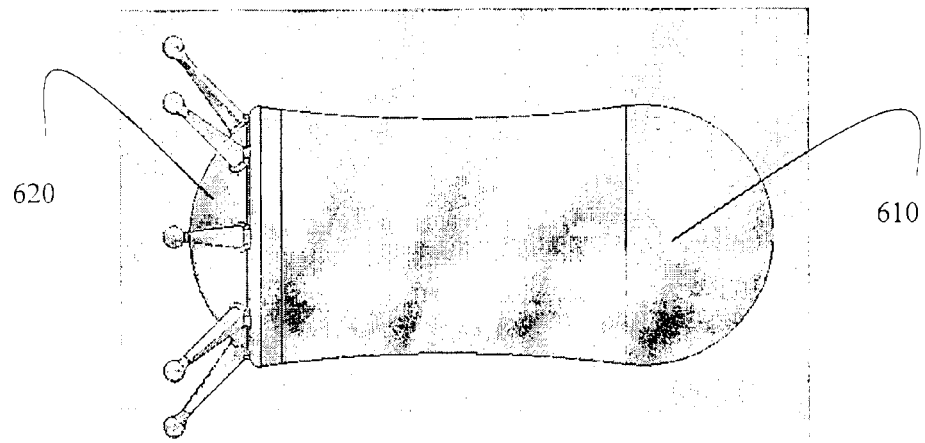

Reference is now made to FIGS. 6a-6b which illustrates a mechanism that is increasing its outer diameter with an increase in the pressure inside the device.

The rounded side portion (numerical reference 610) is receiving the intravaginal pressure and the rod shaped left side portion (numerical reference 620) is exerting the pressure on the vaginal wall.

This design uses a mechanism that is increasing its outer diameter with an increase in the pressure inside the device.

The rods on the surface of the device change their configuration and increase the device diameter.

FIG. 6a illustrates the mechanism is the non-applying pressure configuration and FIG. 6b illustrates the mechanism is the applying pressure configuration.

Figure 7A:
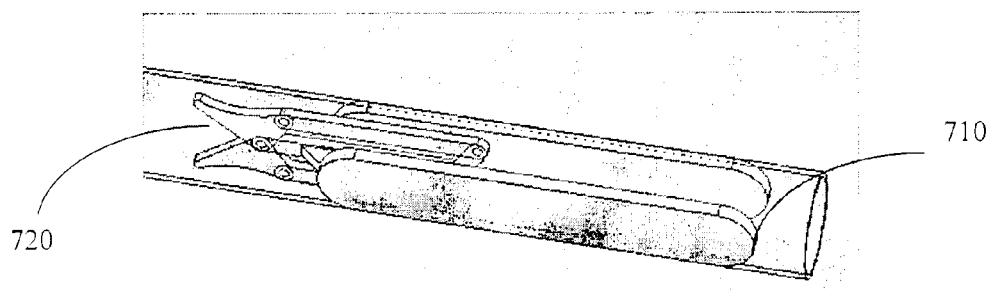
FIGS. 7a-7b illustrate another embodiment of the present invention, in which the device is shaped as a multi-directional clothes peg.
Figure 7B:
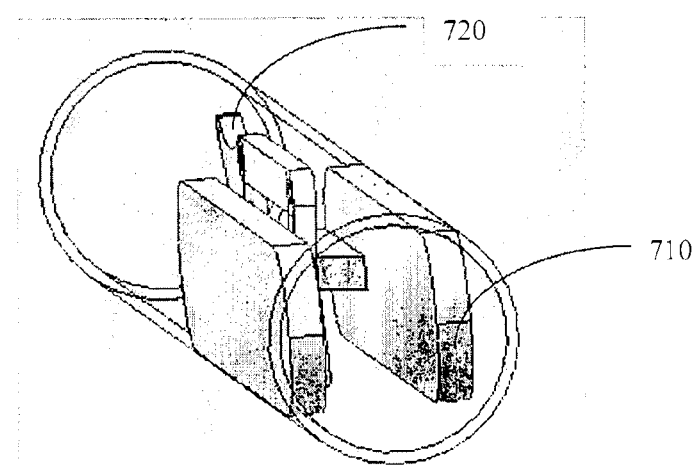

Reference is now made to FIGS. 7a-7b which illustrates another embodiment of the present invention, in which the device is shaped as a multi-directional clothes peg.

The mechanism comprises a proximal portion and a distal portion, interconnected by a main longitudinal axis. Both of said proximal portion and a distal portion are coupled by a hinge or transmission mechanism along said longitudinal axis, adapted to transform force and\or displacement from the proximal part to the distal part.

By providing said mechanism, compressive force of the distal portion results in a broadening (stretching) forces of the proximal portion.

In other words, inward displacement of the portion which is proximal to the vagina would cause an outward displacement and force in the distal part of the vagina.

One example of such a device could be a unidirectional or a multidirectional clothes peg.

According to said embodiment, said deformable state and said un-deformable state of either said deformable distal portion or said deformable proximal portion is obtained by a change in said deformable distal portion or said deformable proximal portion. The change is selected from a group consisting of size, shape, orientation, and position and any combination thereof. The left side portion 710 is e.g., the receiving of the intravaginal pressure and right side portion (numerical reference 720) is exerting the pressure on the vaginal wall.

Once pressure is applied to portion 710, said force is redirected to the right side portion 720, thus (just like a clothes peg) the right side portion 720 applies pressure on the vaginal wall. According to another embodiment, said deformable distal portion or said deformable proximal portions are rigid part-hinge-rigid parts.

Figure 8A:
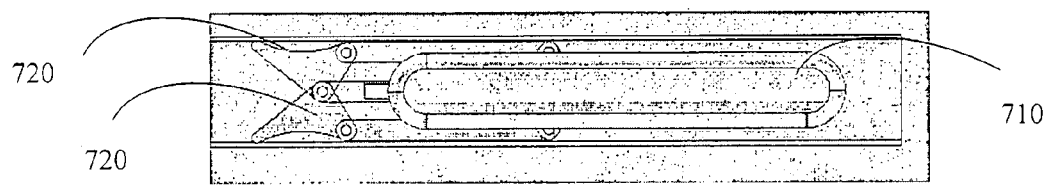
FIGS. 8a-8c illustrate the same embodiment disclosed above, in which a directional mechanical device is provided.
Figure 8B:
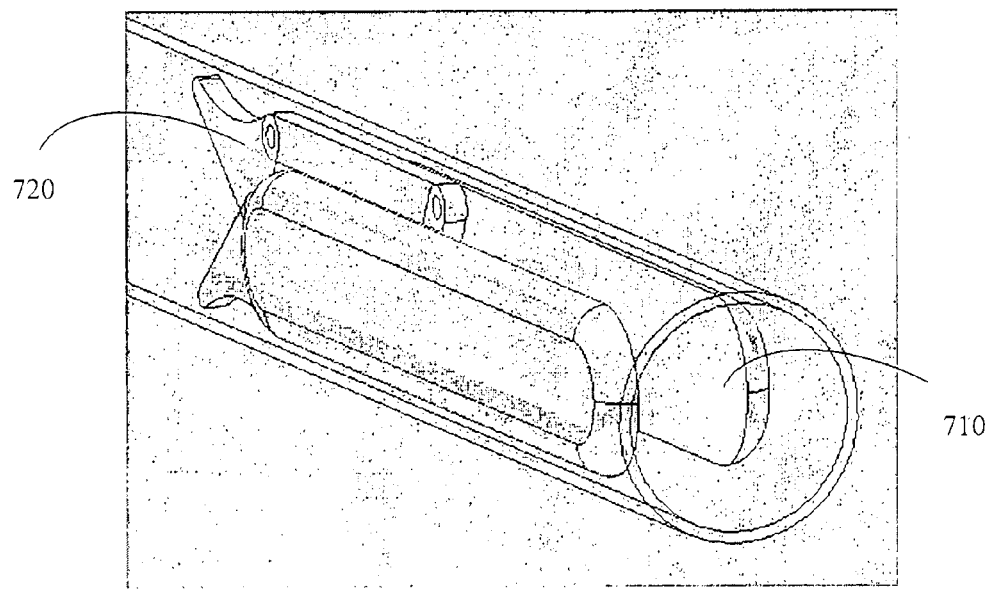
Figure 8C:
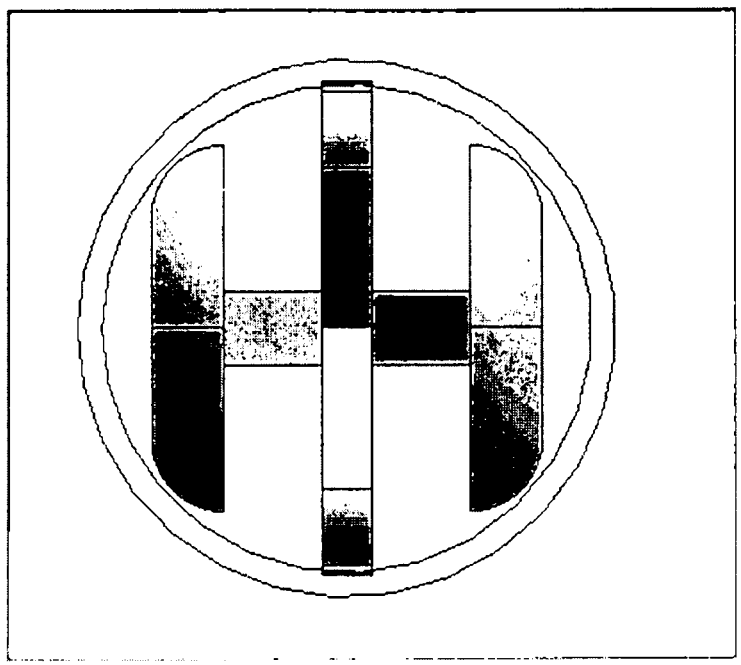

Reference is now made to FIGS. 8a-8c which illustrate the same embodiment disclosed above, in which a directional mechanical device is provided.

FIG. 8a illustrates the above mentioned embodiment in the closed configuration. FIG. 8b illustrates the above mentioned embodiment in the partly open formation.

FIG. 8c illustrates a cross sectional view of the same.

As described in FIGS. 7a-7b, when pressure is applied to the right side portion 710 (namely the elongated planes) the right side portion 720 (namely the triangular shaped pieces) change direction so as to increase device diameter and apply pressure. Reference is now made to FIGS. 9a-9d which another mechanism for the redirection of the pressure applied.

According to said embodiment, right side portion 910 comprises plurality of parallel rods 911, all of which are coupled to a unified coupling point 912 at one side to a plurality of triangular shaped elements 921 on the left side portion 920.

All of said triangular shaped elements 921 are also coupled at a single coupling point 922. Thus, when pressure is applied to the plurality of parallel rods 911, the same are being brought into closer proximity. By means of the unified coupling point 912 the pressure is redirected to the single coupling point 922 so as to re-orient the triangular shaped elements 921.

Said re-orientation of the triangular shaped elements 921 is utilized to increase the diameter of the device (thereby to apply pressure on the vaginal wall).

Figure 9A:
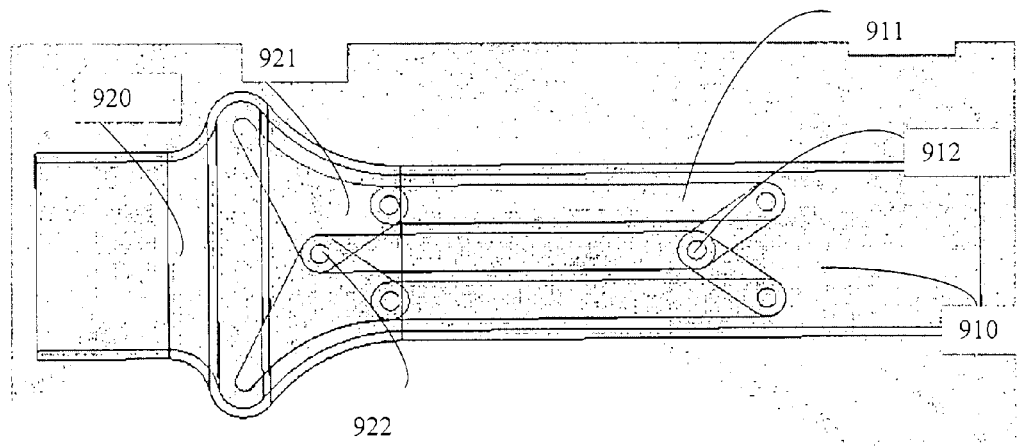
FIGS. 9a-9d illustrate another mechanism for the redirection of the pressure applied.

FIG. 9a illustrates the above mentioned embodiment in the open configuration (namely, in the configuration in which the triangular shaped elements 921 increase the diameter of the device and apply pressure on the vaginal wall.

Figure 9B:
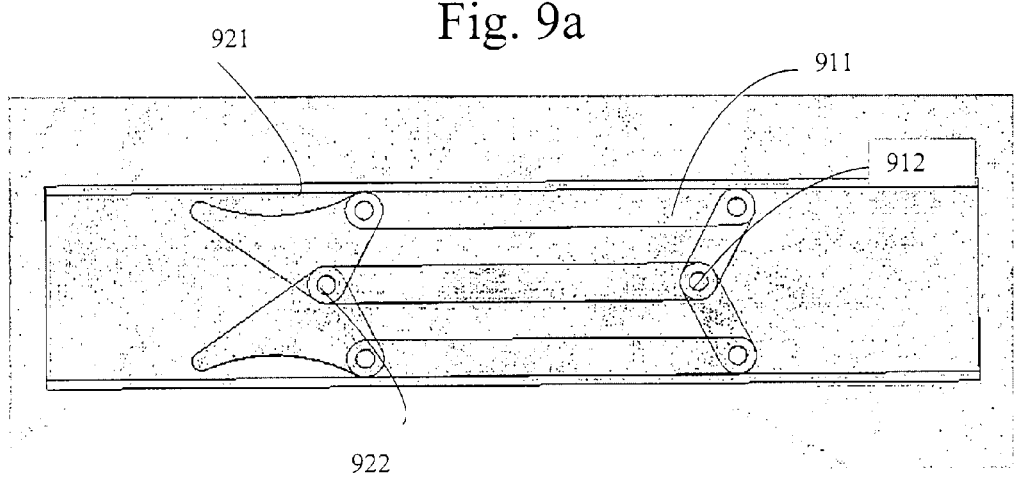
Figure 9C:
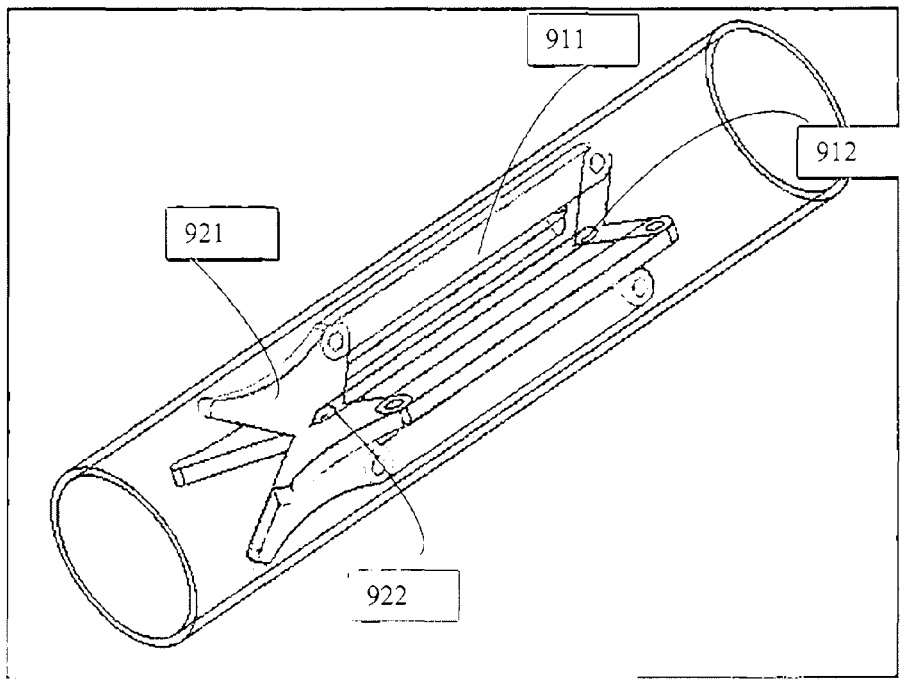
Figure 9D:
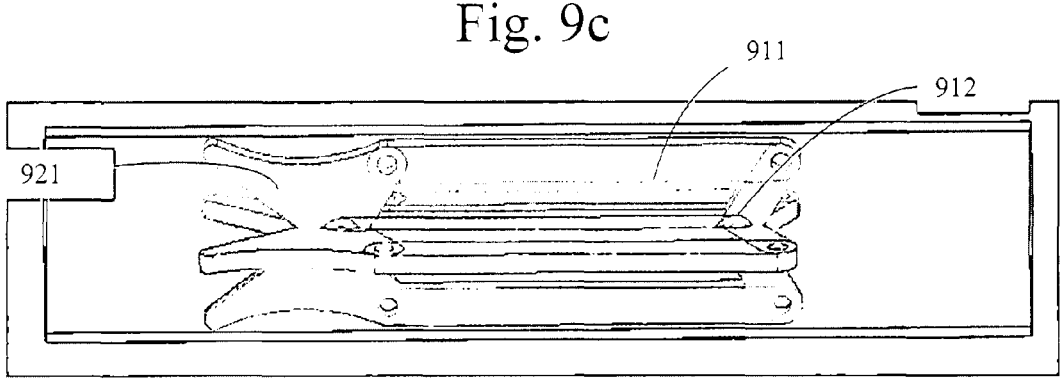

FIGS. 9b-9d illustrate the embodiment described above in the close configuration (namely, in which triangular shaped elements 921 do not apply pressure on the vaginal wall).

Figure 10A:
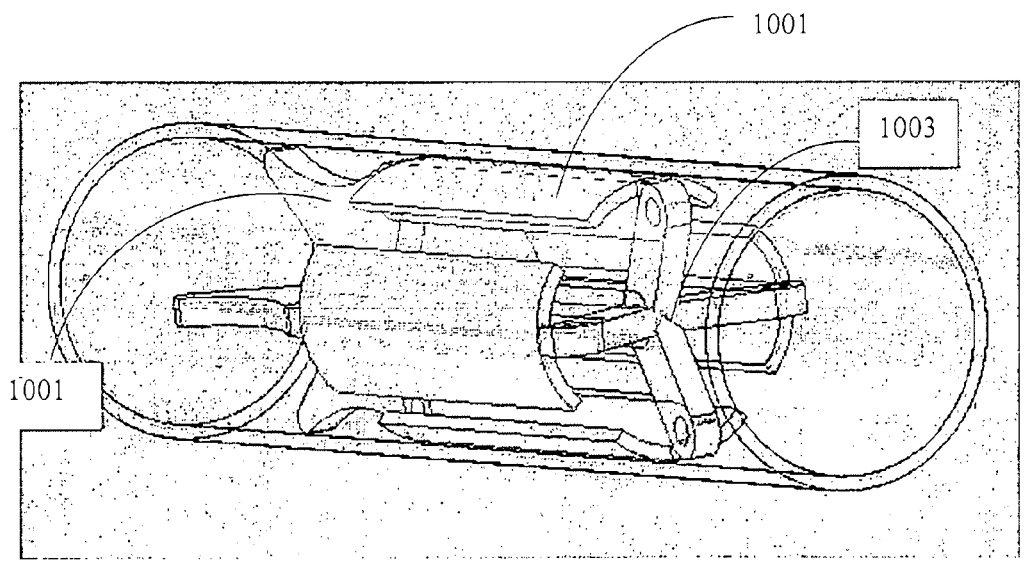
FIGS. 10a-10b illustrate another mechanism for the redirection of the pressure applied.
Figure 10B:
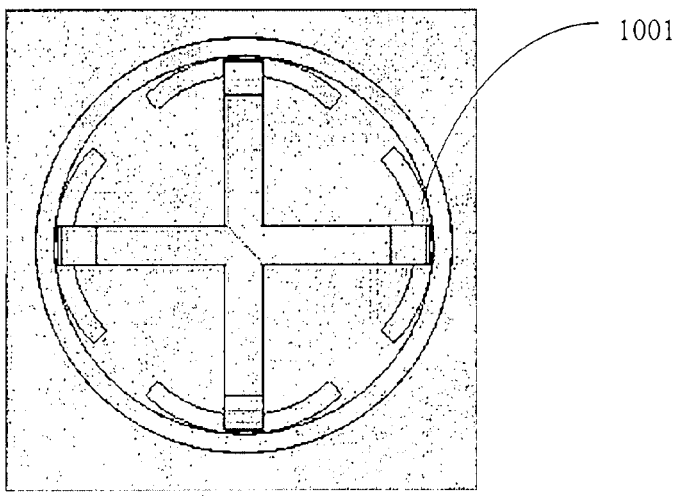

Reference is now made to FIGS. 10a-10b which another mechanism for the redirection of the pressure applied.

In this embodiment, the same mechanism as described above is utilized but in a different design. In FIGS. 10a-10b rounded plates 1001 are used.

One pressure is applied on the plurality of plates 1001 in the right side of the device, the pressure is redirected to the triangular shaped parts 1002, which results in an increase in device diameter.

As before, the plurality of plates 1001 are coupled together (coupling point is referred as 1003), the same as the triangular shaped parts 1002.

Once pressure is applied to the plates 1001 the same is retransferred from the plates (right side) to the triangular shaped parts 1002 (left side) so as to increase the diameter of the device and thus, apply pressure on the vaginal wall.

FIG. 10b illustrates cross sectional view of the same.

It is another object of the present invention to provide a method of treating urinary incontinence, comprising steps of
a. providing an intra-vaginal device for controlling urinary incontinence, said device comprises;
  i. a deformable distal portion designed to be placed in the subvesical region of the vagina; said deformable distal portion is characterized by a deformable state and an un-deformable state;
  ii. a deformable proximal portion designed to be placed in the suburethral portion of the vagina; said deformable proximal portion is characterized by a deformable state and an un-deformable state;
  iii. at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state;
b. inserting said device into the vagina such that said distal portion is located in the subvesical region and said proximal portion is located in the suburethral region; and,
c. sensing intra-vaginal pressure;
d. if said pressure is above predetermined threshold, said proximal portion of said device is activated, thereby applying pressure on the urethra such that urinary incontinence is treated.

It is another object of the present invention to provide a method of treating urinary incontinence, comprising steps of
a. providing an intra-vaginal device for controlling urinary incontinence, said device comprises;
  i. an inflatable distal portion designed to be placed in the subvesical region of the vagina, said distal portion in fluid contact with a reservoir constructed of a material that is essentially non-deformable under pressure; and,
  ii. a proximal portion designed to be placed in the suburethral portion of the vagina, said proximal portion in physical contact with said reservoir; wherein said distal portion is in its inflated state and adapted to be activated upon deflation of said distal portion;
b. inserting said device into the vagina such that said distal portion is located in the subvesical region and said proximal portion is located in the suburethral region; and,
c. sensing intra-vaginal pressure;
d. if said pressure is above predetermined threshold, said device is activated, thereby applying pressure on the urethra such that urinary incontinence is treated.

It is another object of the present invention to provide the methods as defined above, wherein said step of activation of said device further comprising step of activating said proximal portion.

It is another object of the present invention to provide the methods as defined above, wherein said step of activation additionally comprising step of changing at least one of its size, shape, orientation, and position.

It is another object of the present invention to provide the methods as defined above, wherein said change is in at least one of the size, shape, orientation, and position of said proximal portion is of sufficient magnitude to apply pressure on the urethra and at least partially close the same.

It is another object of the present invention to provide the methods as defined above, wherein said proximal portion is inflatable and in fluid contact with said reservoir.

It is another object of the present invention to provide the methods as defined above, further comprising step of providing said reservoir with a piston within the same.

It is another object of the present invention to provide the methods as defined above, additionally comprising step of cantilevering said reservoir to said distal portion.

It is another object of the present invention to provide the methods as defined above, additionally comprising step of providing said proximal with a movable portion, and further comprising a guide, such that said proximal portion is free to move along said guide when said distal portion is in its deflated state but not when said distal portion is in its inflated state.

It is another object of the present invention to provide the methods as defined above, additionally comprising step of providing said device wherein at least one of the length and the width of said reservoir may be altered and then fixed at the altered value prior to insertion of said device into the vagina.

It is another object of the present invention to provide the methods as defined above, additionally comprising step of providing said device wherein at least one of the length and the width of said device may be altered and then fixed at the altered value prior to insertion of said device into the vagina.

It is another object of the present invention to provide the methods as defined above, additionally comprising step of activating said proximal portion upon increase of the intra-vaginal pressure, intra-abdominal, contraction of the pelvic floor muscles or any combination thereof above a threshold value.

It is another object of the present invention to provide the methods as defined above, additionally comprising step of activating said proximal portion to at least a base level, and activated to a higher level upon increase of the intra-vaginal pressure, intra-abdominal, contraction of the pelvic floor muscles or any combination thereof above a threshold value.

It is another object of the present invention to provide the methods as defined above, additionally comprising step of providing constant pressure over a predetermined portion of its area, and a variable pressure over the remainder of its area by said proximal portion.

It is another object of the present invention to provide the methods as defined above, additionally comprising step of providing, by said proximal portion, at least one selected from a group consisting of constant pressure, variable pressure, non-continuous pressure, homogeneous, non-homogeneous pressure.

It is another object of the present invention to provide the methods as defined above, wherein activation of said proximal portion induces backflow from the urethra to the urinary bladder.

It is another object of the present invention to provide the methods as defined above, further comprising step of providing pulsed activation of said proximal portion.

It is another object of the present invention to provide the methods as defined above, further comprising step of measuring the intra-vaginal pressure, intra-abdominal, contraction of the pelvic floor muscles or any combination thereof by at least one pressure sensor.

It is another object of the present invention to provide the methods as defined above, further comprising a control mechanism in contact with said pressure sensor, said control mechanism adapted to activate said proximal portion when the intra-vaginal pressure, intra-abdominal, contraction of the pelvic floor muscles or any combination thereof exceeds a predetermined threshold value.

It is another object of the present invention to provide the methods as defined above, wherein said predetermined threshold value is the urethral pressure.

It is another object of the present invention to provide the methods as defined above, additionally comprising step of contacting the outer surface of said distal portion with substantially the entire circumference of the vaginal wall.

It is another object of the present invention to provide the methods as defined above, additionally comprising step of contacting the outer surface of said distal portion with the vaginal wall in a plurality of separate locations.

It is another object of the present invention to provide the methods as defined above, additionally comprising step of shaping said proximal portion to at least partially surround the urethra.

It is another object of the present invention to provide the methods as defined above, additionally comprising step of providing said device with an absorbent material.

It is another object of the present invention to provide the methods as defined above, additionally comprising step of placing said absorbent material at one of the longitudinal ends of said device.

It is another object of the present invention to provide the methods as defined above, additionally comprising step of completely surrounding said device with said absorbent material substantially.

It is another object of the present invention to provide the methods as defined above, additionally comprising step of sealing said device with a biocompatible material.

It is another object of the present invention to provide the methods as defined above, additionally comprising step of configuring said device as a tampon.

It is another object of the present invention to provide the methods as defined above, additionally comprising step of constructing said device is from shape memory material selected from a group consisting of Nitinol; electro-active polymers or any combination thereof.

It is another object of the present invention to provide the methods as defined above, additionally comprising step of providing said device with at least one diaphragm adapted sense-vaginal pressure, intra-abdominal, contraction of the pelvic floor muscles or any combination thereof and to apply pressure on said urethra.

It is another object of the present invention to provide the methods as defined above, additionally comprising step of constructing said diaphragm of shape memory material, electro-active polymers or any combination thereof.

It is another object of the present invention to provide a method for rehabilitation of stress urinary incontinence, comprising:
  a. obtaining an intra-vaginal device for controlling urinary incontinence;
  b. inserting said device into the vagina such that said distal portion is located in the subvesical region and said proximal portion is located in the suburethral region; and,
  c. contracting at least a portion of the pelvic muscles, whereby said proximal portion applies pressure on said urethra and at least partially closes the same;
wherein said pelvic muscles are strengthened.

It is another object of the present invention to provide the methods as defined above, further including a step of holding said pelvic muscles in their contracted position for a predetermined length of time.

It is another object of the present invention to provide the methods as defined above, wherein said step of providing a obtaining an intra-vaginal device for controlling urinary incontinence additionally comprising step of providing said device with: (a) a deformable distal portion designed to be placed in the subvesical region of the vagina; said deformable distal portion is characterized by a deformable state and an un-deformable state; (b) a deformable proximal portion designed to be placed in the suburethral portion of the vagina; said deformable proximal portion is characterized by a deformable state and an un-deformable state; (c) at least one deformation controlling mechanism interconnecting said distal portion and said proximal portion; said deformation controlling mechanism is adapted to reversibly transform said distal portion and said proximal portion from said deformable state to said un-deformable state; and from said un-deformable state to said deformable state.

It is another object of the present invention to provide the methods as defined above, wherein said step of providing a obtaining an intra-vaginal device for controlling urinary incontinence additionally comprising step of providing said device with: (a) an inflatable distal portion designed to be placed in the subvesical region of the vagina, said distal portion in fluid contact with a reservoir constructed of a material that is essentially non-deformable under pressure; and, (b) a proximal portion designed to be placed in the suburethral portion of the vagina, said proximal portion in physical contact with said reservoir; wherein said distal portion is in its inflated state and adapted to be activated upon deflation of said distal portion.

It is another object of the present invention to provide the methods as defined above, additionally comprising step of constructing said device is from shape memory material selected from a group consisting of Nitinol; electro-active polymers or any combination thereof.

It is another object of the present invention to provide the methods as defined above, additionally comprising step of providing said device with at least one diaphragm adapted sense-vaginal pressure, intra-abdominal, contraction of the pelvic floor muscles or any combination thereof and to apply pressure on said urethra.

It is another object of the present invention to provide the methods as defined above, additionally comprising step of constructing said diaphragm of shape memory material, electro-active polymers or any combination thereof.

It is lastly an object of the present invention to provide the methods as defined above, additionally comprising step of configuring said device as a tampon.

According to another embodiment of the present invention, the device is used for treating at least one selected from a group consisting of menstrual pain, interstitial cystitis, pelvic pain, chronic pelvic pain, painful bladder syndrome or any combination thereof.

A well known theory that relates to pain is the Pain Gate Control Theory. The Pain Gate Control Theory is based on the fact that small diameter nerve fibers carry pain stimuli through a 'gate mechanism' but larger diameter nerve fibers going through the same gate can inhibit the transmission of the smaller nerves carrying the pain signal. Chemicals released as a response to the pain stimuli also influence whether the gate is open or closed for the brain to receive the pain signal.

This lead to the theory that the pain signals can be interfered with by stimulating the periphery of the pain site, the appropriate signal-carrying nerves at the spinal cord, or particular corresponding areas in the brain stem or cerebral cortex.

It is generally recognized that the 'Pain gate' can be shut by stimulating nerves responsible for carrying the touch signal (mechanoreceptors) which enables the relief of pain through the application of pressure applied to the area.

Thus, according to one embodiment of the present invention, the application of the pressure by the device of the present invention, menstrual pain, interstitial cystitis, pelvic pain, chronic pelvic pain, painful bladder syndrome can be treated.

According to another embodiment, a unilateral valve can be utilized.

The valve will be positioned in between the deformable distal portion and the deformable proximal portion. The valve is characterized by at least two configurations. An open configuration in which the same enables the reversible transformation of distal portion and said proximal portion from said deformable state to said un-deformable state; and from said un-deformable state to said deformable state; and a closed configuration in which the same prevents the deformation.

According to said embodiment, the valve is maintained closed for a predetermined amount of time (i.e., the same will prevent the deformation of either one of the distal or proximal portion; by, e.g., preventing the fluid from flowing for a specific amount of time).

According to another embodiment, the valve is self operated. Namely, it is pre-programmed to be reconfigured from the open configuration to the closed one.

According to another embodiment, the valve is externally operated. Namely, it is reconfigured from one state to the other by an external stimulus.

According to another embodiment, said external stimulus is selected from magnetic force, electrical stimulus, electromagnetic stimulus and any combination thereof.

According to another embodiment, when utilizing a magnetic force to externally operate the valve, a magnet that is reversibly coupled to the underwear of the patient can be utilized. The magnet is adapted to close the valve when the underwear are worn and releases the valve when the underwear is off.

Furthermore, the valve can be operated electrically using a remote control.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

We claim:

1. An intra-vaginal device for controlling urinary incontinence, the device comprising:
   deformable inflatable distal and proximal portions designed to be placed in a subvesical region and a suburethral portion of a vagina of a female subject, respectively, said distal and proximal portions having deformed and un-deformed states; and
   at least one deformation controlling mechanism disposed between said distal and proximal portions, said at least one deformation controlling mechanism configured, in response to application of pressure on said distal portion, to transform said proximal portion to the deformed state of said proximal portion, wherein the deformed state of said proximal portion causes said proximal portion to apply pressure on a wall of the vagina and on a urethra of said female subject,
   wherein said distal portion, said proximal portion, and said at least one deformation controlling mechanism: (a) are all structured to be completely inserted into the vagina of the female subject, and (b) are all configured to utilize only gas stored within them to facilitate the deformation of said distal portion and said proximal portion.

2. The device according to claim 1 further configured to maintain a baseline pressure until the pressure applied on the distal portion is increased to a predetermined amount of pressure.

3. The device according to claim 1 wherein the deformation controlling mechanism is non-deformable under vaginal pressure.

4. The device according to claim 1 further configured to restore the states of the distal and proximal portions upon relaxation of the pressure applied on the distal portion.

5. The device according to claim 1 wherein the proximal portion is spherical or ellipsoidal in shape.

6. The device according to claim 1 wherein the proximal portion is shaped and configured to at least partially surround or encompass the urethra, wherein the shape of the proximal portion is configured to cause the pressure applied by the proximal portion on the urethra to squeeze the urethra from a bottom of the urethra and sides of the urethra.

7. The device according to claim 1 further comprising: one or more pressure sensors adapted to measure an intra-vaginal pressure; and activation means configured to deform the proximal portion to a predetermined extent depending on the pressure measured by said one or more pressure sensors.

8. The device according to claim 1 wherein the proximal portion is configured to apply constant pressure over a predetermined portion of the area of the proximal portion, and a variable pressure over a remainder of the area of the proximal portion.

9. The device according to claim 1 wherein the proximal portion is configured to induce backflow of urine in a direction of the urinary bladder whenever the proximal portion is transformed to the deformed state.

10. The device according to claim 1 further comprising absorbent material, said absorbent material provided in at least one of the following: the distal portion; the proximal portion; or their combination.

11. A method of treating urinary incontinence in a female subject, the method comprising:
- providing a device having deformable distal and proximal portions, said distal and proximal portions comprise a deformed state and an un-deformed state, and at least one deformation controlling mechanism disposed between said distal and proximal portions, wherein said distal portion, said proximal portion, and said at least one deformation controlling mechanism are all configured to utilize only gas stored within them;
- introducing said device via an opening of a vagina into a vaginal cavity of said female subject and advancing said device inside the vaginal cavity until said device is completely inside the vaginal cavity;
- positioning the distal portion in a subvesical region and the proximal portion in a suburethral region; and
- applying pressure on a vaginal wall and on a urethra of said female subject by transforming said proximal portion to the deformed state of said proximal portion in response to an inner body pressure applied to said distal portion,
- wherein said transforming said proximal portion to the deformed state of said proximal portion uses said at least one deformation controlling mechanism and said gas.

* * * * *